(12) United States Patent
Cho et al.

(10) Patent No.: US 11,432,747 B2
(45) Date of Patent: Sep. 6, 2022

(54) BIO SENSOR, METHOD FOR MANUFACTURING BIO SENSOR, AND APPARATUS FOR MEASURING BIO SIGNALS

(71) Applicant: SAMSUNG ELECTRONICS CO., LTD., Suwon-si (KR)

(72) Inventors: Chul-ho Cho, Yongin-si (KR); Seong-je Cho, Suwon-si (KR); Jin-hong Min, Suwon-si (KR); Kyoung-jin Moon, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 336 days.

(21) Appl. No.: 16/614,576

(22) PCT Filed: May 17, 2018

(86) PCT No.: PCT/KR2018/005677
§ 371 (c)(1),
(2) Date: Nov. 18, 2019

(87) PCT Pub. No.: WO2018/216956
PCT Pub. Date: Nov. 29, 2018

(65) Prior Publication Data
US 2020/0170552 A1 Jun. 4, 2020

(30) Foreign Application Priority Data
May 22, 2017 (KR) .................. 10-2017-0062826

(51) Int. Cl.
*A61B 5/145* (2006.01)
*A61B 5/1486* (2006.01)
(Continued)

(52) U.S. Cl.
CPC ...... *A61B 5/14532* (2013.01); *A61B 5/14865* (2013.01); *A61B 5/1473* (2013.01);
(Continued)

(58) Field of Classification Search
CPC ............ A61B 5/14532; A61B 5/14865; A61B 5/14546; A61B 5/1473; A61B 5/6848;
(Continued)

(56) References Cited

U.S. PATENT DOCUMENTS

| | | | |
|---|---|---|---|
| 5,800,420 A * | 9/1998 | Gross | ................... A61K 9/7023 604/890.1 |
| 5,807,375 A | 9/1998 | Gross et al. | |

(Continued)

FOREIGN PATENT DOCUMENTS

| | | |
|---|---|---|
| JP | 10508518 A | 8/1998 |
| JP | 2004-180773 A | 7/2004 |

(Continued)

OTHER PUBLICATIONS

Communication dated Jun. 29, 2021 issued by the Korean Intellectual Property Office in application No. English 10-2017-0062826 Translation.

(Continued)

*Primary Examiner* — Kaylee R Wilson
*Assistant Examiner* — Meghan R Kumar
(74) *Attorney, Agent, or Firm* — Sughrue Mion, PLLC

(57) ABSTRACT

Disclosed is an apparatus for measuring bio signals. The apparatus for measuring bio signals includes: a sensor module configured to include a needle sensor to be inserted into the skin; and a main body to which the sensor module is separably coupled, and which is configured to include a controller controlling the sensor module to measure a bio signal through the needle sensor, once the sensor module is coupled.

15 Claims, 21 Drawing Sheets

(51) Int. Cl.
*A61B 5/1473* (2006.01)
*A61B 5/00* (2006.01)

(52) U.S. Cl.
CPC ......... *A61B 5/14546* (2013.01); *A61B 5/6848* (2013.01); *A61B 2560/0223* (2013.01); *A61B 2560/0443* (2013.01); *A61B 2562/125* (2013.01)

(58) Field of Classification Search
CPC .... A61B 2560/0223; A61B 2560/0443; A61B 2562/125
See application file for complete search history.

(56) References Cited

U.S. PATENT DOCUMENTS

| | | |
|---|---|---|
| 5,820,622 A | 10/1998 | Gross et al. |
| RE43,039 E | 12/2011 | Brister et al. |
| 8,160,669 B2 | 4/2012 | Brauker et al. |
| 8,167,852 B2 | 5/2012 | Quan et al. |
| 8,206,297 B2 | 6/2012 | Kamath et al. |
| 8,971,981 B2 | 3/2015 | Yodfat et al. |
| 9,662,440 B2 | 5/2017 | Yodfat et al. |
| 10,357,191 B2 | 7/2019 | Di Resta et al. |
| 10,448,872 B2 | 10/2019 | Wolfe et al. |
| 2008/0215035 A1* | 9/2008 | Yodfat .................. A61M 5/158 604/513 |
| 2013/0296664 A1* | 11/2013 | Frey ................... A61B 5/14532 600/309 |
| 2013/0313130 A1* | 11/2013 | Little ..................... C12Q 1/006 205/792 |
| 2015/0282711 A1 | 10/2015 | Thomas et al. |
| 2017/0224912 A1 | 8/2017 | Yodfat et al. |
| 2017/0261388 A1* | 9/2017 | Ma .......................... G16Z 99/00 |

FOREIGN PATENT DOCUMENTS

| | | |
|---|---|---|
| JP | 2011507555 A | 3/2011 |
| JP | 2013-521942 A | 6/2013 |
| JP | 5754195 B2 | 7/2015 |
| JP | 2016-516472 A | 6/2016 |
| KR | 10-2010-0025509 A | 3/2010 |
| KR | 10-2016-0041667 A | 4/2016 |
| KR | 1020160115689 A | 10/2016 |
| WO | 96/14026 A1 | 5/1996 |
| WO | 2016/153313 A1 | 9/2016 |

OTHER PUBLICATIONS

Search Report dated Aug. 17, 2018, issued by the International Searching Authority in International Application No. PCT/KR2018/005677 (PCT/ISA/210).
Written Opinio dated Aug. 17, 2018, issued by the International Searching Authority in International Application No. PCT/KR2018/005677 (PCT/ISA/237).

\* cited by examiner

BIO SENSOR, METHOD FOR MANUFACTURING BIO SENSOR, AND APPARATUS FOR MEASURING BIO SIGNALS

TECHNICAL FIELD

The disclosure relates to a bio sensor, a method for manufacturing a bio sensor, and an apparatus for measuring bio signals.

BACKGROUND ART

As human life is extended, interest in a health care apparatus for health care is increasing. Recently, various types of apparatuses for measuring bio signals that may be used by a user to measure his/her bio signals by himself/herself to check a health condition have been developed and used.

Such an apparatus for measuring bio signals may be implemented in a form of, for example, a wearable device. Specifically, the apparatus for measuring bio signals may be implemented in a form of a smart bracelet, a smart watch, smart glasses, or the like. As the user wears the apparatus for measuring bio signals, various types of sensors may come into contact with the skin of the user to measure and analyze bio signals.

Further, recently, an apparatus (for example, a glucometer) for measuring bio signals that measures a state (for example, a blood glucose level or a hormone level) of body fluid or blood of the user has been used to more precisely detect bio signals. In the case of such an apparatus for measuring bio signals, the user needs to collect body fluid or blood by using a separate lancet and bring the collected blood into contact with (put the collected blood on) a separate sensor provided in the apparatus for measuring bio signals to measure bio signals.

DISCLOSURE

Technical Problem

However, the apparatus for measuring bio signals that is implemented in a form of a wearable device according to the related art has a limitation in a type of bio signal to be measured and precision, and in the case of the apparatus for measuring bio signals using body fluid or blood, such as a glucometer, body fluid or blood of the user needs to be collected each time the measurement is performed, which is disadvantageous.

Technical Solution

An object of the disclosure is to provide an apparatus for measuring bio signals capable of continuously measuring bio signals of a user.

Another object of the disclosure is to provide an apparatus for measuring bio signals, of which a needle sensor may be easily replaced.

Still another object of the disclosure is to provide a bio sensor with improved usability and manufacturability, and a method for manufacturing a bio sensor.

According to an embodiment of the disclosure, an apparatus for measuring bio signals includes: a sensor module configured to include a needle sensor to be inserted into the skin; and a main body to which the sensor module is separably coupled and which is configured to include a controller controlling the sensor module to measure a bio signal through the needle sensor, once the sensor module is coupled.

The sensor module may include a first terminal portion connected to the needle sensor and the main body may include a second terminal portion electrically connecting the first terminal portion and the controller to each other through coupling of the sensor module.

The main body may have a coupling groove which is formed in a bottom surface of the main body and into which the sensor module is inserted, and the second terminal portion may be disposed in the coupling groove.

The main body may have a coupling hole penetrating through the main body to allow the sensor module to be inserted, the first terminal portion may be disposed at a side surface of the sensor module, and the second terminal portion may be disposed at an inner circumferential surface of the coupling hole.

The sensor module may include a first magnet portion, and the main body may include a second magnet portion attached to the first magnet portion to allow the sensor module inserted into the main body to be in position.

The main body may include at least one auxiliary sensor disposed in a bottom surface of the main body and coming into contact with the skin.

The at least one auxiliary sensor may be any one of a thermister, a plurality of metal electrodes, an infrared (IR) sensor, or an optical sensor.

The main body may further include an antenna transmitting bio information acquired through the controller to the outside.

The needle sensor may include first and second electrode portions to be inserted into the skin, and the controller may measure an electric current flowing between the first electrode portion and the second electrode portion.

According to another embodiment of the disclosure, a bio sensor to be inserted into the skin includes: a first electrode portion of which one end is sharp; and a second electrode portion configured to face the first electrode portion with a space therebetween and of which one end is sharp.

The bio sensor may further include at least one spacer disposed between the first electrode portion and the second electrode portion.

The bio sensor may further include a support member separably disposed between the first electrode portion and the second electrode portion and supporting the first and second electrode portions.

The first and second electrode portions may be formed by folding a thin film substrate to make first and second electrode patterns printed on the thin film substrate at a predetermined interval face each other.

The first electrode portion may include a first substrate, a first electrode layer, and a dielectric layer which are sequentially laminated, the second electrode portion may include a second substrate, a second electrode layer, and a reagent layer which are sequentially laminated, and the first and second electrode portions may be laminated to make the dielectric layer and the reagent layer be in contact with each other.

The first electrode portion may have a first connector groove and include a first connector inserted into the first connector groove and electrically connected to the first electrode layer, and the second electrode portion may have a second connector groove and include a second connector inserted into the second connector groove and electrically connected to the second electrode layer.

A cross section of the bio sensor taken along a direction perpendicular to a length direction may have a concentric circle shape in which the first substrate, the first electrode layer, the dielectric layer, the reagent layer, the second electrode layer, and the second substrate are sequentially laminated.

The bio sensor may further include a reagent layer coupled to any one of the first and second electrode portions.

The reagent layer may include at least one of a glucose oxidase, a glucose dehydrogenase, a cholesterol oxidase, a cholesterol esterase, a lactate oxidase, an ascorbate oxidase, an alcohol oxidase, an alcohol dehydrogenase, a bilirubin oxidase, or a sugar dehydrogenase.

According to still another embodiment of the disclosure, a method for manufacturing a bio sensor, includes: printing at least one pair of electrode patterns on one surface of a thin film substrate; disposing a spacer on at least one of the pair of electrode patterns; cutting the thin film substrate in a shape of the pair of electrode patterns; folding the cut thin film substrate.

In the printing, at least one pair of first and second electrode patterns of which one ends are spaced apart from each other at a predetermined interval may be printed, the one ends being sharp and facing each other, and in the folding, the thin film substrate may be folded at a portion between the one end of the first electrode pattern and the one end of the second electrode pattern to make the first electrode pattern and the second electrode pattern face each other.

DESCRIPTION OF DRAWINGS

FIG. 10b is a plan view illustrating a modified example of the bio sensor illustrated in FIG. 10a.

FIG. 10c is a plan view illustrating another modified example of the bio sensor illustrated in FIG. 10a.

FIG. 10d is a plan view illustrating still another modified example of the bio sensor illustrated in FIG. 10a.

FIG. 14b is a side cross-sectional view of the bio sensor illustrated in FIG. 14a.

FIG. 14c is a perspective view illustrating a modified example of the bio sensor illustrated in FIG. 14a.

BEST MODE

Figure 1:
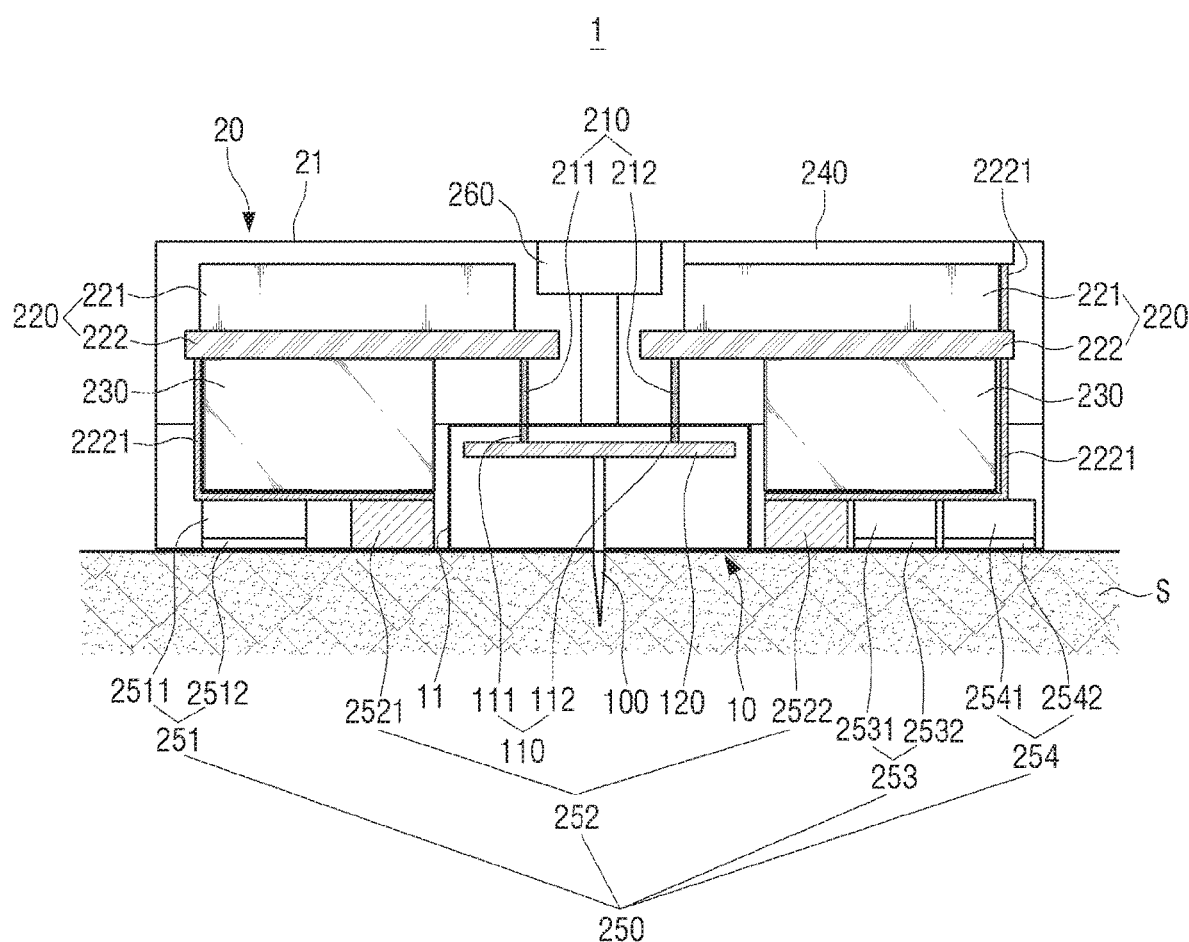
FIG. 1 is a side cross-sectional view of an apparatus for measuring bio signals according to an embodiment of the disclosure.

Hereinafter, embodiments of the disclosure will be described in detail with reference to the accompanying drawings. Embodiments to be described below will be described on the basis of embodiments most appropriate for understanding technical features of the disclosure, and these embodiments do not limit the technical features of the disclosure, but exemplify that the disclosure may be implemented like these embodiments.

Therefore, the disclosure may be variously modified without departing from the technical scope of the disclosure through embodiments to be described below, and these modifications will be to fall within the technical scope of the disclosure. In addition, to assist in the understanding of embodiments to be described below, components performing the same operations and related components in the respective embodiments will be denoted by the same or similar reference numerals throughout the accompanying drawings. Further, the accompanying drawings are not illustrated to scale, but sizes of some of components may be exaggerated to assist in the understanding of the disclosure.

Figure 2:
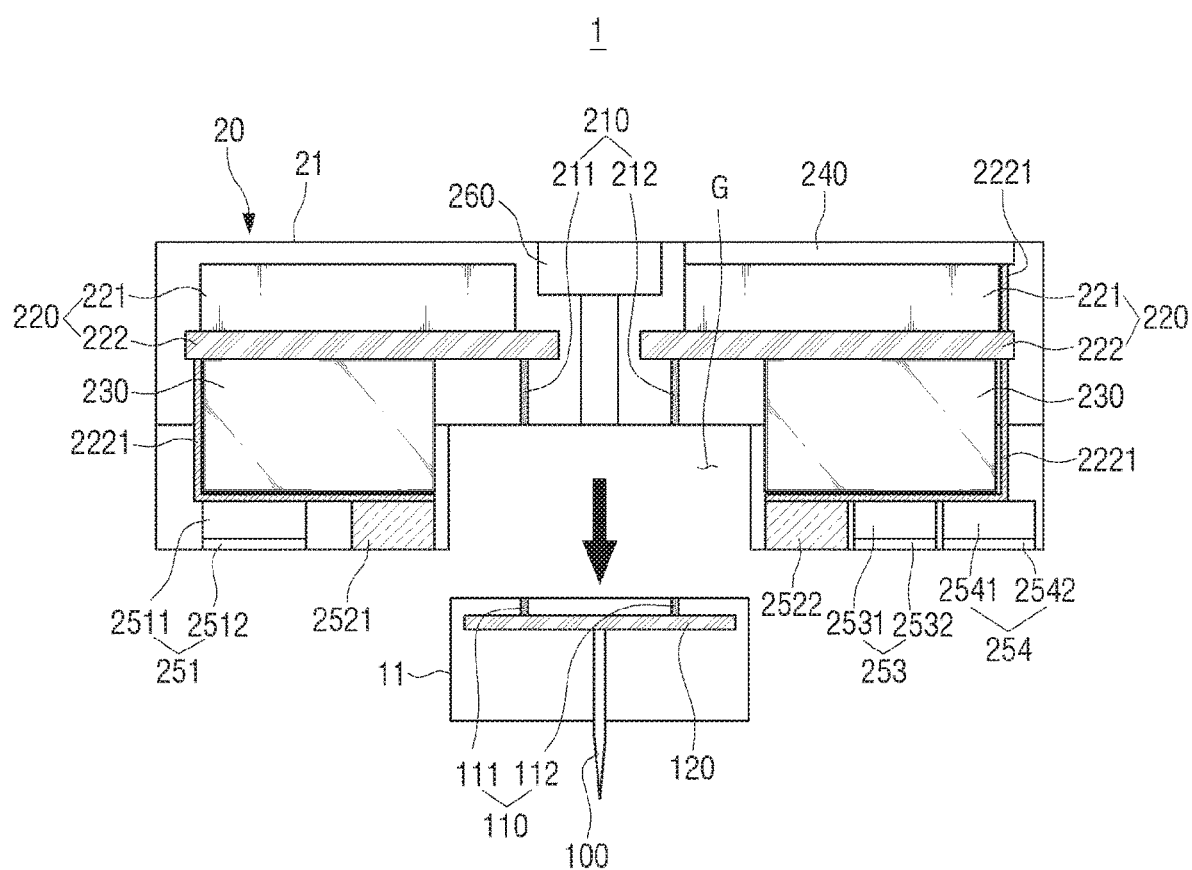
FIG. 2 is a side cross-sectional view of the apparatus for measuring bio signals illustrated in FIG. 1 in a state in which a sensor module and a main body are separated from each other.

FIG. 1 is a side cross-sectional view of an apparatus 1 for measuring bio signals according to an embodiment of the disclosure, and FIG. 2 is a side cross-sectional view of the apparatus 1 for measuring bio signals illustrated in FIG. 1 in a state in which a sensor module 10 and a main body 20 are separated from each other.

FIG. 1 illustrates a state in which the apparatus 1 for measuring bio signals is attached to the skin S of a user to measure a bio signal of the user, for convenience of explanation. In this state, a needle sensor 100 is inserted into the skin S and a bottom surface of the main body 20 comes into contact with the skin S.

Hereinafter, a structure of the apparatus 1 for measuring bio signals according to an embodiment of the disclosure will be described in detail with reference to FIGS. 1 and 2.

As illustrated in FIGS. 1 and 2, the apparatus 1 for measuring bio signals includes the sensor module 10 including the needle sensor 100 to be inserted into the skin S, and the main body 20 to which the sensor module 10 is separably coupled.

The needle sensor 100 is disposed at a central portion of the sensor module 10 and protrudes from the sensor module 10 to be insertable into the skin S.

The sensor module 10 includes a hexahedral or cylindrical module housing 11, and the needle sensor 100 is coupled in the module housing 11 and a distal end portion of the needle sensor 100 protrudes from a central lower end portion of the module housing 11.

Further, it is preferable that the distal end portion of the needle sensor 100 protruding toward an area below the module housing 11 is sharp for easy insertion into the skin S.

The needle sensor 100 may directly come into contact with body fluid or blood in the body by being inserted into the skin S, and thus the apparatus 1 for measuring bio signals may measure a state of the body fluid or blood.

For example, the needle sensor 100 may include first and second electronic portions (not illustrated) to be inserted into the skin S. The first electrode portion and the second electrode portion are electrodes corresponding to each other, and the needle sensor 100 may be an electrochemical sensor measuring a ratio of components contained in body fluid or blood, a concentration of a specific component, and the like, by measuring an electric current flowing between the first electrode and the second electrode. Further, the needle sensor 100 may be implemented by a conventional needle-type bio sensor.

As a specific example, the needle sensor 100 may be one of various types of bio sensors capable of measuring a concentration of a specific component contained in blood or body fluid. For example, the needle sensor 100 may be a bio sensor capable of detecting a concentration (blood glucose) of glucose, a concentration of a specific hormone, a concentration of nicotine, a concentration of a specific antigen or antibody, or the like.

Hereinafter, the case where the needle sensor 100 is a bio electrical impedance analysis (BIA) type electrochemical sensor, which is an electrochemical sensor capable of measuring impedance by supplying an electric current into the body after being inserted into the skin S, and by measuring a voltage caused by the electric current. However, the needle sensor 100 may be implemented by various bio sensors according to the related art, in addition to the BIA type electrochemical sensor.

Further, the needle sensor 100 may be an enzymatic sensor (for example, a glucose sensor) in which any one of the first electrode portion or the second electrode portion includes a reagent layer such as an enzyme layer, or may be a non-enzymatic sensor without a separate reagent layer.

A specific embodiment of the needle sensor 100 according to the disclosure will be described later with reference to FIGS. 9 to 14*c*.

The sensor module 10 includes a first terminal portion 110 connected to the needle sensor 100.

The first terminal portion 110 is a component that may be electrically connected to a second terminal portion 210 of the main body 20 as described later. For example, the first terminal portion 110 may include first and second terminals 111 and 112 disposed at an upper end portion of the sensor module 10, but may also include only a single terminal.

Further, the sensor module 10 may further include a connection plate 120 disposed in the module housing 11, and the needle sensor 100 and the first and second terminals 111 and 112 may be connected to one another through the connection plate 120. The connection plate 120 may be, for example, a flexible printed circuit board (FPCB).

As illustrated in FIGS. 1 and 2, an upper end of the needle sensor 100 is coupled to a lower end portion of the connection plate 120 in the module housing 11, and the first and second terminals 111 and 112 each having one end coupled to an upper end portion of the connection plate 120 may each have the other end exposed or protruding to the outside from an upper surface of the module housing 11. As a result, the needle sensor 100 and the first terminal portion 110 may be electrically connected to each other, and the first terminal portion 110 may be electrically connected to the second terminal portion 220 of the main body 20.

The main body 20 includes a main body housing 21 forming an exterior and the main body housing 21 may have a hexahedral or cylindrical shape.

The main body 20 has a coupling groove G formed at a central portion (a central portion of a lower end portion of the main body housing 21) of a lower end portion of the main body 20 and into which and to which the sensor module 10 may be inserted and coupled. The coupling groove G has a shape corresponding to a shape of the module housing 11 to allow the sensor module 10 to be inserted into and coupled to a lower side of the main body 20.

Further, as illustrated in FIG. 1, the bottom surface of the main body 20 may come into contact with the skin S, and for this, the bottom surface of the main body 20 may be directly attached to the skin S or may be fixed in a state of being in contact with the skin S by using a fixing member such as a separate strap.

Therefore, the bottom surface of the main body 20 comes into contact with the skin S in a state in which the sensor module 10 is coupled to the main body 20, and the needle sensor 100 of the sensor module 10 inserted into the coupling groove G may be inserted into the skin S.

As a specific example, the user may press the sensor module 10 toward the skin S at a desired position on the skin to insert the needle sensor 100 into the skin, and then may attach or fix the main body 20 to the skin S so that the sensor module 10 may be inserted into the coupling groove G. Further, the user may couple the module sensor 10 to the main body 20 and then press the main body 20 to which the module sensor 10 is coupled at a desired position on the skin, thereby inserting the needle sensor 100 and attaching or fixing the main body 20 to the skin S, at the same time.

The main body 20 includes the second terminal portion 210 electrically connected to the first terminal portion 110 through coupling of the sensor module 10, and a controller 220 controlling the apparatus 1 for measuring bio signals.

As the sensor module 10 is coupled to the main body through the coupling groove G, the second terminal portion 210 may come into contact with the first terminal portion 110, and as a result, the second terminal portion 210 may be electrically connected to the first terminal portion 110.

To this end, the second terminal portion 210 may be disposed in the coupling groove G. Specifically, the second terminal portion 210 may have one end exposed or protruding to the outside in the coupling groove G to thereby be connected to the first terminal portion 110.

Further, the second terminal portion 210 may be connected to the controller 220 disposed in the main body 20, and may electrically connect the first terminal portion 110 and the controller 220 to each other through coupling of the sensor module 10. Therefore, the controller 220 may control the sensor module 10 to measure a bio signal through the needle sensor 100.

For example, the second terminal portion 210 may include fourth and fifth terminals 211 and 212 as illustrated in FIGS. 1 and 2.

The fourth and fifth terminals 211 and 212 of the second terminal portion 210 may correspond to the first and second terminals 111 and 112 of the first terminal portion 110, respectively. Therefore, in the case where the sensor module 10 is inserted into the coupling groove G to be coupled to the main body 20, the first terminal 111 and the fourth terminal 211 may be connected to each other, and the second terminal 112 and the fifth terminal 212 may be connected to each other. To this end, it is preferable that a disposition layout of the first and second terminals 111 and 112 and a disposition layout of the fourth and fifth terminals 211 and 212 correspond to each other or are the same as each other.

The above-described structures of the first and second terminals 111 and 112 of the first terminal portion 110 and the fourth and fifth terminals 211 and 212 of the second terminal portion 210 have been described as an example of the first and second terminal portion 110 and 210. The first and second terminal portions 110 and 210 may each include a single terminal or three or more terminals. Further, detailed structures of the first terminal portion 110 and the second terminal portion 210 may be variously changed as long as the first terminal portion 110 and the second terminal portion 210 may be electrically connected to each other through coupling between the sensor module 10 and the main body 20.

The controller 220 may include a printed circuit board (PCB) 222 and at least one electronic component 221 mounted on the printed circuit board 222. Further, the electronic component 221 may be a microprocessor, a microcomputer, a central processing unit (CPU), or the like, and may be implemented by various types of electronic components capable of controlling the main body 20 and the sensor module 10 coupled to the main body 20.

Further, the above-described second terminal portion 210 may be electrically connected to the printed circuit board 222, and as a result, the controller 220 and the second terminal portion 210 may be electrically connected to each other, and the controller 220 and the needle sensor 100 may be electrically connected to each other through the first terminal portion 110 connected to the second terminal portion 210.

Further, a battery 230 functioning as a power supply portion may be mounted on the printed circuit board 222. The battery 230 may supply power to the main body 20 including the controller 220. Therefore, the apparatus 1 for measuring bio signals may be operated for a predetermined period in a state of being attached to the skin S of the user without a separate power cable for receiving power from an external power supply.

Further, the power supplied from the battery 230 may be supplied to the sensor module 10 through the controller 220 and the second terminal portion 210. As a result, the needle sensor 100 may be operated as an electrochemical sensor by way of example.

Further, the battery 230 may be a primary battery detachably coupled in the main body 20, or may be a secondary battery including a charge connector (not illustrated) that may be connected to an external power supply.

As described above, the sensor module 10 is separably coupled to the main body 20. Therefore, only the sensor module 10 may be replaced without replacing the main body 20, and once a predetermined period elapses after the needle sensor 100 is inserted into the skin S, only the sensor module 10 may be easily replaced to prevent contamination by the needle sensor 100, or the like.

As such, the needle sensor 100 to be inserted into the skin S is included in the sensor module 10 separably coupled to the main body 20, and the first terminal portion 110 of the sensor module 10 coupled to the main body 20 is connected to the second terminal portion 210 of the main body 20, such that bio signal measurement and bio information acquisition by using the needle sensor 100 are performed under the control of the controller 220 in the main body 20. Therefore, it is possible to easily replace the needle sensor 100 at low cost by separating only the sensor module 10 from the main body 20 and replacing the sensor module 20. Further, components that need not be replaced, such as the main body 20, the controller 220 included in the main body 20, and the battery 230 may be semi-permanently used.

Further, the sensor module 10 includes a minimal number of components such as the needle sensor 100, and the first terminal portion 110 for connection to the main body 20, and the controller 220 for controlling the sensor module 10 and the battery 230 for supplying power are disposed in the main body 20 and electrically connected to the sensor module 10 through the second terminal portion 210. Therefore, the sensor module 10 according to an embodiment of the disclosure may be configured to be compact.

As a result, it is possible to simplify a coupling structure between the sensor module 10 and the main body 20 in the apparatus 1 for measuring bio signals according to an embodiment of the disclosure, decrease an entire height of the apparatus 1 for measuring bio signals that is attached and fixed to the skin S, reduce manufacturing costs and the number of manufacturing processes of the sensor module 10 that needs to be periodically replaced, and reduce replacement costs of the sensor module 10 and operation and maintenance costs of the apparatus 1 for measuring bio signals.

Further, the main body 20 may further include at least one auxiliary sensor 250 disposed in the bottom surface of the main body 20 to come into contact with the skin S or to be adjacent to the skin S.

The at least one auxiliary sensor 250 may be disposed in the main body 20 and connected to the printed circuit board 222 through at least one connection member 2221, and may be controlled by the controller 220 to measure a bio signal by coming into contact with the skin S.

The auxiliary sensor 250 may additionally detect various types of bio signals by coming into contact with the skin S, and thus it is possible to improve accuracy in measurement of a bio signal detected through the needle sensor 100 and accuracy of bio information acquired through the bio signal measured through the needle sensor 100.

For example, the at least one auxiliary sensor 250 may be any one of a thermister, a plurality of metal electrodes, an infrared (IR) sensor, or an optical sensor, and the number of auxiliary sensors 250 may be plural.

As illustrated in FIGS. 1 and 2, the auxiliary sensor 250 may include, for example, first to fourth auxiliary sensors 251 to 254.

As a specific example, the first auxiliary sensor 251 may be a thermister 251 including a thermister main body 2511 and a metal plate 2512. As heat (body temperature) of the skin S is transferred to the thermister main body 2511 through the metal plate 2512 that is in contact with the skin S, a temperature of the skin S may be measured.

Further, the second auxiliary sensor 252 may be an impedance measuring sensor 252 including a first metal electrode 2521 and a second metal electrode 2522 that come into contact with the skin S, and may measure a change in impedance of epidermis of the skin S.

Further, the third auxiliary sensor 253 may be an IR sensor 253 including an IR sensor main body 2531 and a cover window 2532 that comes into contact with the skin S, and may measure a temperature of the skin S.

Further, the fourth auxiliary sensor 254 may be an optical sensor 254 including an optical sensor main body 2541 and a cover window 2542 that comes into contact with the skin S, and may measure a change in blood flow in the body by coming into contact with the skin S. Further, the cover window 2542 may maintain a predetermined measuring distance required between the optical sensor main body 2541 and the skin S.

However, the at least one auxiliary sensor 250 may include various types of sensors that is disposed to come into contact with the skin S or to be adjacent to the skin S and is capable of detecting various types of bio signals, in addition to the thermister, the impedance measuring sensor, the IR sensor, and the optical sensor described above.

As the main body 20 includes at least one auxiliary sensor 250, it is possible to improve accuracy in measurement of a bio signal detected through the needle sensor 100, and perform an additional measurement of various types of bio signals, in addition to the measurement of the bio signal through the needle sensor 100. Further, the auxiliary sensor 250 is disposed in the main body 20, and thus the auxiliary sensor 250 included in the body 20 may be continuously used even in the case where the sensor module 10 is replaced.

Further, the main body 20 may further include a sensor module releasing pin 260.

The sensor module releasing pin 260 may be disposed at a central portion of the main body 20 and penetrate through the main body 20, and the sensor module releasing pin 260 may be movable so that a lower end portion of the sensor module releasing pin 260 protrudes toward a lower side of the coupling groove G.

Therefore, in the case where the sensor module 10 needs to be replaced in a state in which the needle sensor 100 of the sensor module 10 is inserted into the skin S as illustrated in FIG. 1, the user may press the sensor module releasing pin 260 to make the lower end portion of the sensor module releasing pin 260 push the upper end portion of the sensor module 10. By doing so, the main body 20 may be easily separated from the sensor module 10 and the skin S, and the sensor module 10 may be separated from the skin S after separating the main body 20 from the skin S.

Further, the needle sensor 100 may include a support member (not illustrated) supporting the needle sensor to maintain rigidity at the time of being inserted into the skin S, and the sensor module releasing pin 260 may separate the support member from the needle sensor 100 after the needle sensor 100 is inserted into the skin S and takes the support member out through an upper side of the sensor module releasing pin 260.

Further, the sensor module releasing pin 260 may move so that one end thereof protrudes from the coupling groove G by penetrating through the central portion of the main body 20, and thus it is preferable that the controller 220 and the battery 230 disposed in the main body 20 do not interfere with the sensor module releasing pin 260. For example, the printed circuit board 222 or the battery 230 may have a through-type cylindrical or donut-shaped structure having an opening portion through which the sensor module releasing pin 260 may penetrate, and may have a C-letter shape or a U-letter shape.

The main body 20 may further include an antenna 240 transmitting bio information acquired through the controller 220 to the outside.

The antenna 240 may be disposed in the main body 20 and disposed at an upper end portion of the main body 20 to effectively transmit and obtain a signal. Further, the antenna 240 may be connected to the printed circuit board 222 through at least one connection member 2221.

The antenna 240 may transmit bio information to a mobile device such as a smartphone, a table personal computer (PC), or a smartwatch. As a result, the user may easily check the bio information through the mobile device. Further, the controller 220 may transmit a signal indicating information such as an operation state of the apparatus 1 for measuring bio signals, a power supply state of the battery 230, and a replacement cycle of the sensor module 10 to the mobile device through the antenna 240. Further, the apparatus 1 for measuring bio signals may obtain a control signal for operation of the apparatus 1 for measuring bio signals, or the like from the mobile device through the antenna 240, and the user may easily operate the apparatus 1 for measuring bio signals through the mobile device.

Further, the main body 20 may further include a display (not illustrated) or a speaker (not illustrated) to transfer, to the user, the bio information acquired through the bio signal, in a form of an image or a sound.

Figure 3:
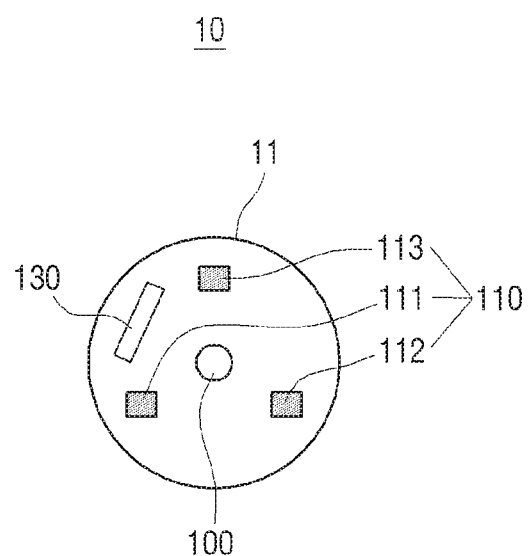
FIG. 3 is a plan view of the sensor module illustrated in FIG. 2.
Figure 4:
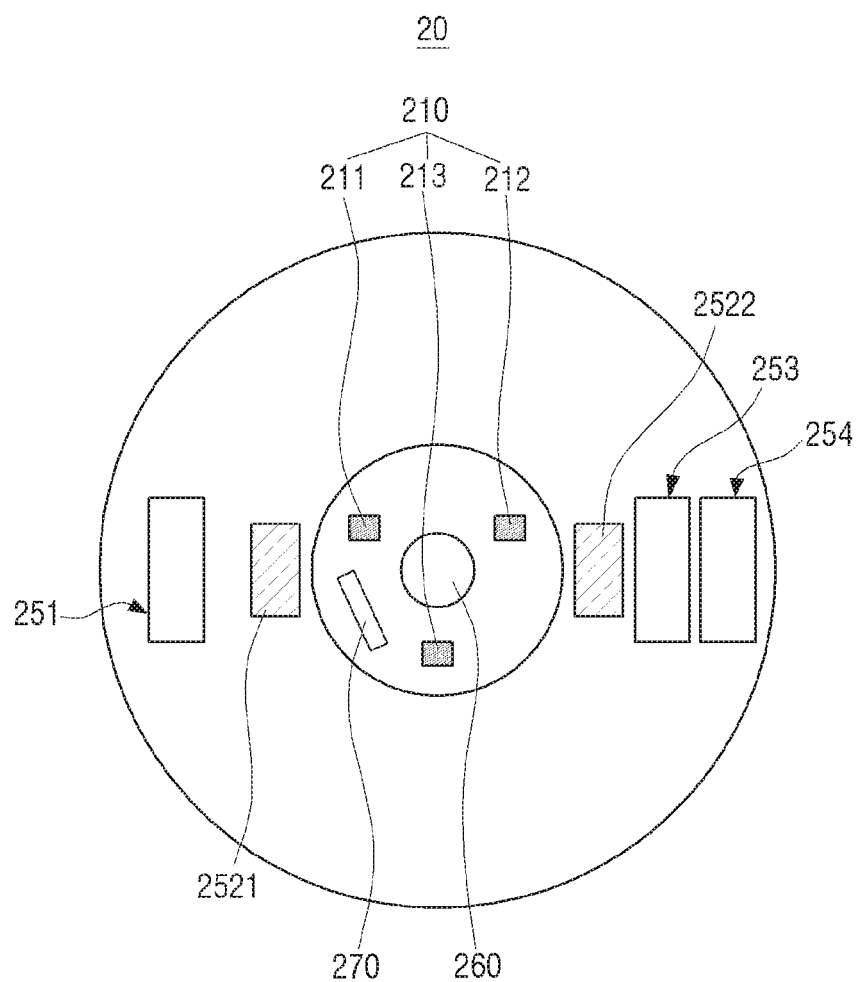
FIG. 4 is a bottom view of the main body illustrated in FIG. 2.

FIG. 3 is a plan view of the sensor module 10 illustrated in FIG. 2, and FIG. 4 is a bottom view of the main body 20 illustrated in FIG. 2. As illustrated in FIGS. 3 and 4, the sensor module 10 and the main body 20 may have a cylindrical shape.

Referring to FIG. 3, one ends of the first and second terminals 111 and 112 may be disposed on an upper portion of the sensor module 10, and a third terminal 113 may be additionally disposed on the upper portion of the sensor module 10.

The first to third terminals 111 to 113 of the first terminal portion 110 may be arranged radially around the needle sensor 100 at predetermined intervals. For example, the first to third terminals 111 to 113 may be arranged around the needle sensor 100 to form a triangle.

Referring to FIG. 4, the first to fourth auxiliary sensors 251 to 254 may be arranged in the bottom surface of the main body 20.

Further, one ends of the fourth and fifth terminals 211 and 212 corresponding to the first and second terminals 111 and 112 may be disposed at an upper portion of the coupling groove G, that is, in a bottom surface of the central portion of the main body 20 in which the coupling groove G is formed, and one end of the a sixth terminal 213 corresponding to the third terminal 113 may be additionally disposed at the upper portion of the coupling groove G.

The fourth to sixth terminals 211 to 213 may be arranged to correspond to the first to third terminals 111 to 113. For example, the fourth to sixth terminals 211 to 213 may be arranged around the main body 20 to form a triangle.

Further, as illustrated in FIGS. 3 and 4, the sensor module 10 includes a first magnet portion 130, and the main body 20 includes a second magnet portion 270 to be attached to the first magnet portion 130 to allow the sensor module 10 inserted into the main body 20 to be in position.

The first magnet portion 130 may be disposed on the upper end portion of the sensor module 10 and may be implemented by at least one magnet.

Further, the second magnet portion 270 may be implemented by a magnet corresponding to the first magnet portion 130 and may be implemented by a magnet of which a shape, the number, and a layout are the same as those of the magnet implementing the first magnet portion 130.

In the case where the first and second magnet portions 130 and 270 each include a single magnet, it is preferable that the first magnet portion 130 is disposed on the upper end portion of the sensor module 10 to be biased from the center of the sensor module 10, that is, the needle sensor 100, to allow the sensor module 10 to be in position at the time of insertion of the sensor module 10 into the coupling groove G of the main body 20.

It is preferable that a shape and a layout of the first magnet portion 130 correspond to those of the second magnet portion 270, respectively. By doing so, the main body 20 and the sensor module 10 may be in position so that the first to third terminals 111 to 113 and the fourth to sixth terminals 211 to 213 are connected to each other, respectively, at the time of coupling between the main body 20 and the sensor module 10.

Specifically, it is preferable that a disposition layout of the one ends of the first to third terminals 111 to 113, and the first magnet portion 130 disposed at the upper end portion of the sensor module 10 corresponds to a disposition layout of the one ends of the fourth to sixth terminals 211 to 213, and the second magnet portion 270 of the main body 20.

The user may easily couple the sensor module 10 and the main body 20 to each other by using the first and second magnet portions 130 and 270 described above.

Figure 5:
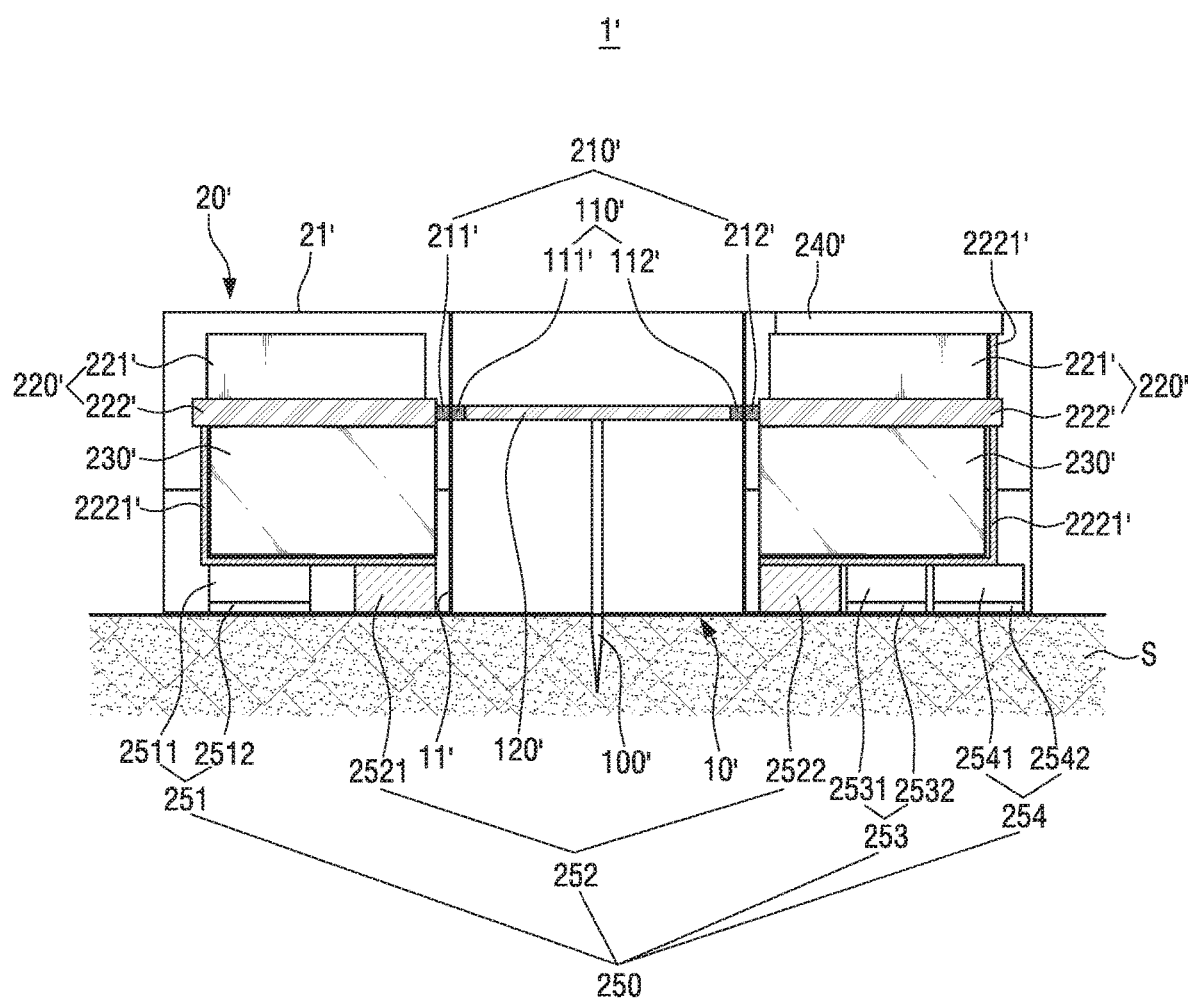
FIG. 5 is a side cross-sectional view of an apparatus for measuring bio signals according to another embodiment of the disclosure.
Figure 6:
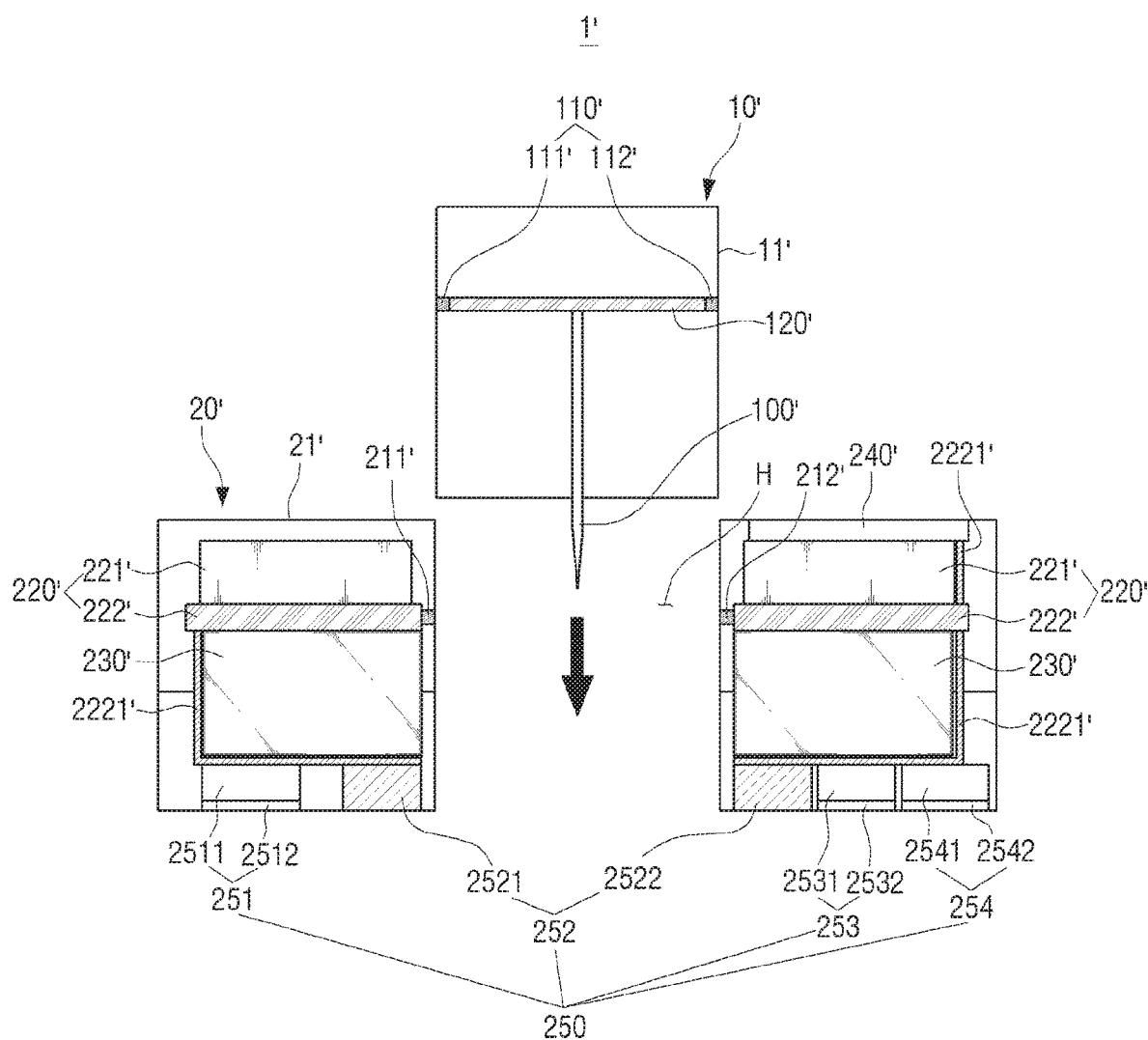
FIG. 6 is a side cross-sectional view of the apparatus for measuring bio signals illustrated in FIG. 5 in a state in which a sensor module and a main body are separated from each other.

FIG. 5 is a side cross-sectional view of an apparatus 1' for measuring bio signals according to another embodiment of the disclosure, and FIG. 6 is a side cross-sectional view of the apparatus 1' for measuring bio signals illustrated in FIG. 5 in a state in which a sensor module 10' and a main body 20' are separated from each other.

Hereinafter, a structure of the apparatus 1' for measuring bio signals according to another embodiment of the disclosure will be described with reference to FIGS. 5 and 6. However, a configuration and a structure of the apparatus 1' for measuring bio signals illustrated in FIGS. and 6 are substantially the same as those of the apparatus 1 for measuring bio signals according to an embodiment of the disclosure described above, and thus a similar or overlapping description will be omitted.

The apparatus 1' for measuring bio signals includes the sensor module 10' including a needle sensor 100' to be inserted into the skin S, and the main body 20' to which the sensor module 10' is separably coupled.

The needle sensor 100' is disposed at a central portion of the sensor module 10' and protrudes from the sensor module 10' to be insertable into the skin S. The sensor module 10' includes a hexahedral or cylindrical module housing 11'.

The needle sensor 100' protrudes from a central lower portion of the module housing 11' so that a distal end portion of the needle sensor 100' may be inserted into the skin S.

The distal end portion of the needle sensor 100' is sharp and a structure of the needle sensor 100' is similar to that of the needle sensor 100 illustrated in FIGS. 1 and 2.

As illustrated in FIGS. 5 and 6, the main body 20' has a coupling hole H formed in a central portion of the main body 20' and vertically penetrating through the main body 20'.

The sensor module 10' may be inserted into the coupling hole H from above the main body 20'.

As a specific example, the user may easily insert the needle sensor 100' into a desired position on the skin S by attaching the main body 20' to a desired position on the skin S and then inserting the sensor module 10' into the coupling hole H, and may instantaneously insert the needle sensor 100' into the skin S by inserting the sensor module 10' into the coupling hole H and then instantaneously pressing the sensor module 10'.

Further, the coupling hole H may penetrate through the central portion of the main body 20'. Therefore, the sensor module 10' may be inserted into the coupling hole H by using a separate shooter (not illustrated) after the main body 20' is attached to the skin S, and the need sensor 100' may be instantaneously inserted into the skin S by the shooter.

Specifically, the distal end portion of the needle sensor 100' protruding toward an area below the sensor module 10' may be instantaneously inserted into the skin S by attaching the main body 20' to a desired position on the skin S, mounting the sensor module 10' on the shooter, placing the shooter above the main body 20', that is, above the coupling hole H, and instantaneously pushing the sensor module 10' downward (toward the skin) by using the shooter.

As such, the main body 20' has the coupling hole H vertically penetrating through the main body 20', and the sensor module 10' is inserted into the skin S from above the main body 20' through the coupling hole H, such that it is possible to more easily insert the needle sensor 100' into the skin S.

Further, it is possible to more accurately insert the needle sensor 100' into the skin S because a position on the skin S into which the needle sensor 100' is to be inserted may be easily confirmed through the coupling hole H in a process of attaching the main body 20' to the skin S.

The sensor module 10' includes a first terminal portion 110' connected to the needle sensor 100', and the first terminal portion 110' includes first and second terminals 111' and 112'.

Further, the sensor module 10' may include a connection plate 120' disposed therein, and the needle sensor 100' and the first and second terminals 111' and 112' may be connected to one another through the connection plate 120'.

As illustrated in FIGS. 5 and 6, the first terminal portion 110' is disposed at a side surface of the sensor module 100', that is, a side surface of the module housing 11', and a second terminal portion 210' of the main body 20' connected to the first terminal portion 110' is disposed at an inner circumferential surface of the coupling hole H.

The main body 20' includes the second terminal portion 210' electrically connected to the first terminal portion 110' through coupling of the sensor module 10', and a controller 220' controlling the apparatus 1' for measuring bio signals.

The controller 220' may include a printed circuit board 222' and at least one electronic component 221' mounted on the printed circuit board 222', and a configuration and a structure of the controller 220' is similar to or the same as the structure of the controller 220 illustrated in FIGS. 1 and 2.

As described above, the first terminal portion 110' of the sensor module 10' is disposed at the side surface of the sensor module 10', and thus the second terminal portion 210' electrically connected to the first terminal portion 110' through coupling of the sensor module 10' is disposed at a position on the inner circumferential surface of the coupling hole H, the position corresponding to the first terminal portion 110'.

Specifically, the first terminal portion 110' includes the first and second terminals 111' and 112' disposed at the side surface of the module housing 11' and exposed or protruding to the outside. Further, the second terminal portion 210' includes third and fourth terminals 211' and 212' corresponding to the first and second terminals 111' and 112', respectively, and the third and fourth terminals 211' and 212' may each have one end exposed or protruding to the outside at the inner circumferential surface of the coupling hole H.

Further, the first terminal portion 110' and the second terminal portion 210' may each include at least one terminal, and structures of the first terminal portion 110' and the second terminal portion 210' may be changed to various structures in which the first terminal portion 110' and the second terminal portion 210' may be electrically connected to each other through coupling between the sensor module 10' and the main body 20' through the coupling hole H.

Further, the main body 20' includes a battery 230' coupled to the printed circuit board 222', and the coupling hole H vertically penetrates the central portion of the main body 20'. Therefore, the controller 220' and the battery 230' disposed in the main body 20' may each have an opening portion penetrating through a central portion thereof and corresponding to the coupling hole H.

Specifically, the printed circuit board 222' and the battery 230' may each have a cylindrical or donut-shaped structure having an opening portion formed in a central portion thereof, and may have a C-letter shape or a U-letter shape.

Further, components such as the controller 220' and the battery 230' disposed in the main body 20' may be disposed to correspond to a shape of the coupling hole H, in the main body 20'.

Further, the main body 20' may include an antenna 240' transmitting bio information acquired through the controller 220' to the outside, and at least one auxiliary sensor 250 disposed in a bottom surface of the main body 20'.

The antenna 240' and the auxiliary sensor 250 may be electrically connected to the printed circuit board 222' through at least one connection member 2221'.

The auxiliary sensor 250 may include first to fourth auxiliary sensors 251 to 254, the first auxiliary sensor 251 may be a thermister 251 including a thermister main body 2511 and a metal plate 2512, the second auxiliary sensor 252 may be an impedance measuring sensor 252 including a first metal electrode 2521 and a second metal electrode 2522 that come into contact with the skin S, the third auxiliary sensor 253 may be an IR sensor 253 including an IR sensor main body 2531 and a cover window 2532 that comes into contact with the skin S, and the fourth auxiliary sensor 254 may be an optical sensor 254 including an optical sensor main body 2541 and a cover window 2542 that comes into contact with the skin S.

However, the auxiliary sensor 250 illustrated in FIGS. 5 and 6 has the same configuration as that of the auxiliary sensor 250 illustrated in FIGS. 1 and 2, and thus, an overlapping description will be omitted.

Figure 7:
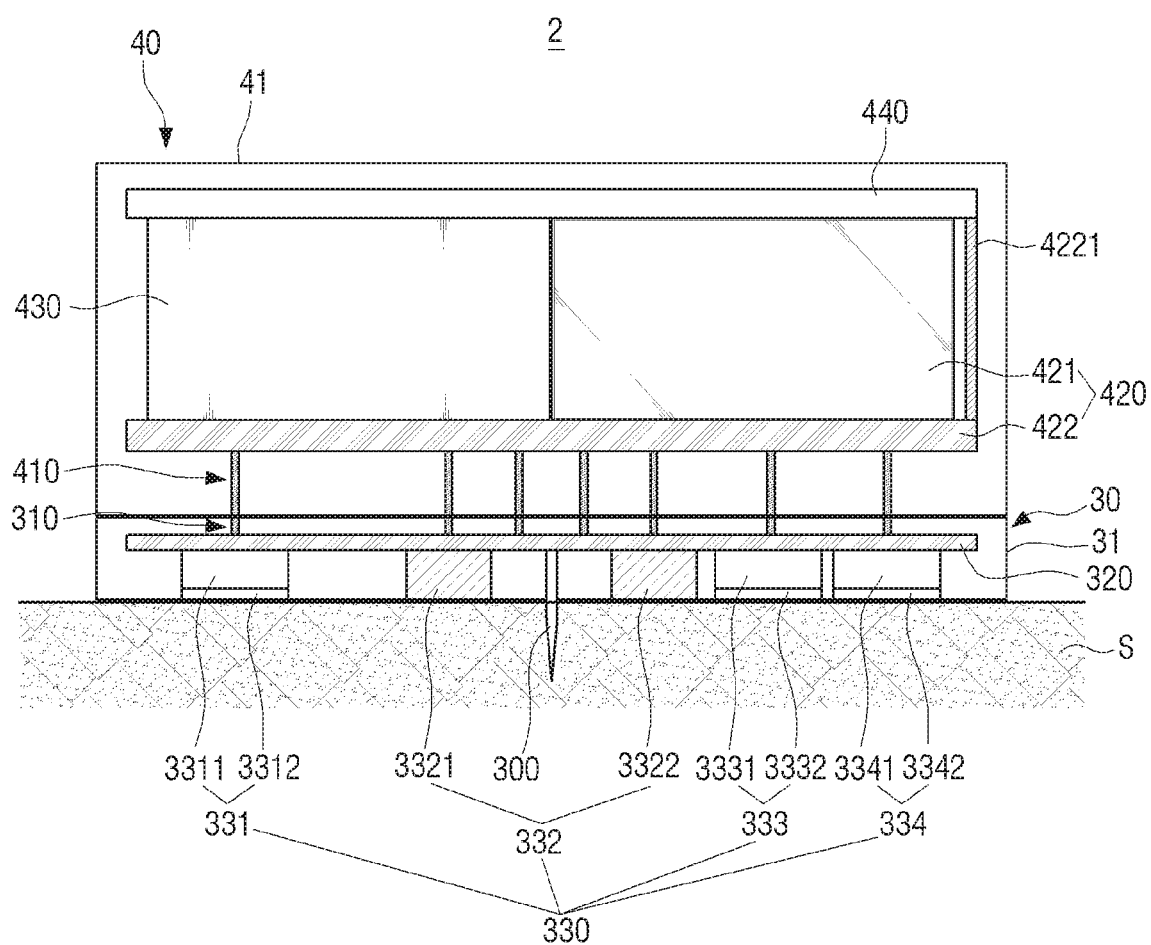
FIG. 7 is a side cross-sectional view of an apparatus for measuring bio signals according to still another embodiment of the disclosure.
Figure 8:
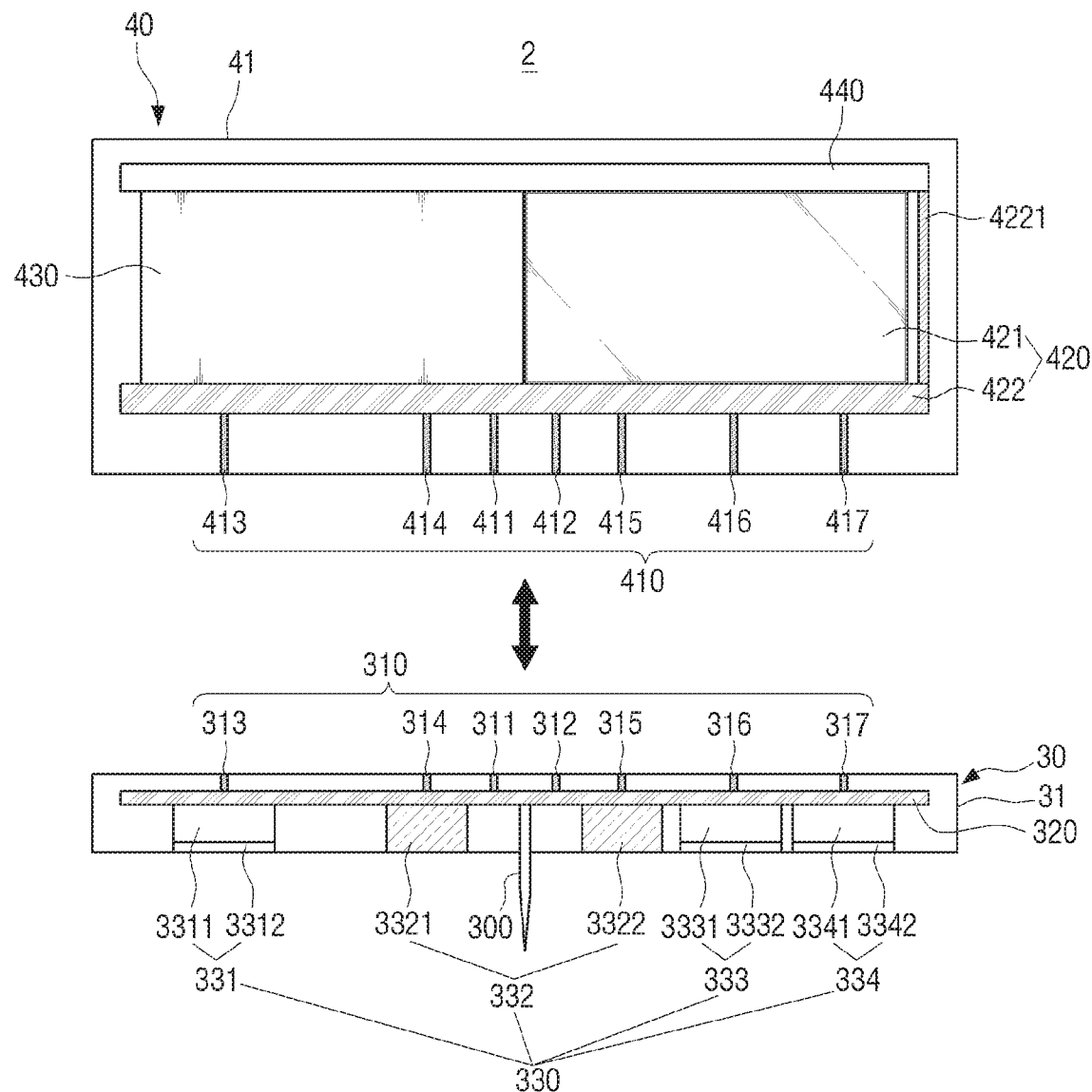
FIG. 8 is a side cross-sectional view of the apparatus for measuring bio signals illustrated in FIG. 7 in a state in which a sensor module and a main body are separated from each other.

FIG. 7 is a side cross-sectional view of an apparatus for measuring bio signals according to still another embodiment of the disclosure, and FIG. 8 is a side cross-sectional view of the apparatus 2 for measuring bio signals illustrated in FIG. 7 in a state in which a sensor module 30 and a main body 40 are separated from each other.

Hereinafter, a structure of the apparatus 2 for measuring bio signals according to still another embodiment of the disclosure will be described with reference to FIGS. 7 and 8. However, a description of a structure of the apparatus 2 for measuring bio signals illustrated in FIGS. 7 and 8 that overlaps with those of the apparatus 1 for measuring bio signals according to an embodiment of the disclosure and the apparatus 1' for measuring bio signals according to another embodiment of the disclosure described above will be omitted, and a difference between the apparatus 2 for measuring bio signals and the apparatuses 1 and 1' for measuring bio signals will be mainly described.

As illustrated in FIGS. 7 and 8, the apparatus 2 for measuring bio signals includes the sensor module 30 including a needle sensor 300 to be inserted into the skin S, and the main body 40 to which the sensor module 30 is separably coupled.

The sensor module 30 may be separably coupled to a lower portion of the main body 40, and a distal end portion of the needle sensor 300 to be inserted into the skin S protrudes toward an area below a hexahedral or cylindrical module housing 31.

Further, the sensor module 30 may further include at least one auxiliary sensor 330 disposed in a bottom surface of the sensor module 30, that is, in a bottom surface of the module housing 31, to come into contact with the skin S or to be adjacent to the skin S.

For example, the at least one auxiliary sensor 330 may include first to fourth auxiliary sensors 331 to 334, and the first to fourth auxiliary sensors 331 to 334 may be the same as the first to fourth auxiliary sensors 251 to 254 illustrated in FIGS. 1 and 2.

Further, the sensor module 30 includes a first terminal portion 310 for connection to the main body 40, and the first terminal portion 310 may include at least one terminal.

For example, the first terminal portion 310 may include first and second terminals 311 and 312 electrically connected to the needle sensor 300, and third to seventh terminals 313 to 317 electrically connected to the first to fourth auxiliary sensors 331 to 334, respectively.

Specifically, the first auxiliary sensor 331 may be a thermister 331 including a thermister main body 3311 and a metal plate 3312, the second auxiliary sensor 332 may be an impedance measuring sensor 332 including a first metal electrode 3321 and a second metal electrode 3322 that come into contact with the skin S, the third auxiliary sensor 333 may be an IR sensor 333 including an IR sensor main body 3331 and a cover window 3332 that comes into contact with the skin S, and the fourth auxiliary sensor 334 may be an optical sensor 334 including an optical sensor main body 3341 and a cover window 3342 that comes into contact with the skin S.

Further, the third terminal 313 may be connected to the first auxiliary sensor 331, the fourth and fifth terminals 314 and 315 may be connected to the first and second metal electrodes 3321 and 3322 of the second auxiliary sensor 332, respectively, the sixth terminal 316 may be connected to the third auxiliary sensor 333, and the seventh terminal 317 may be connected to the fourth auxiliary sensor 334.

The needle sensor 300 and the first to fourth auxiliary sensors 331 to 334 may be connected to the first to seventh terminals 311 to 317 through a connection plate 320.

The main body 40 includes a main body housing 41 forming an exterior, a controller 420 including a printed circuit board 422 on which at least one electronic component 421 is mounted, a battery 430, an antenna 440, and at least one connection portion 4221. However, structures of the main body housing 41, the controller 420, the battery 430, the antenna 440, and the connection portion 4221 are similar to those of the main body housing 11, the controller 220, the battery 230, the antenna 240, and the connection portion 2221 illustrated in FIGS. 1 and 2, and thus an overlapping description will be omitted.

The main body 40 includes a second terminal portion 410 having one end exposed or protruding from a bottom surface of the main body 40.

The second terminal portion 410 may be electrically connected to the first terminal portion 310 through coupling between the sensor module 30 and the main body 40, to electrically connect the sensor module 30 and the controller 420 to each other.

The second terminal portion 410 corresponds to the first terminal portion 310. For example, the second terminal portion 410 may include eighth to fourteenth terminals 411 and 417 corresponding to the first to seventh terminals 311 to 317, respectively.

The eighth to fourteenth terminals 411 to 417 may each have one end exposed at the bottom surface of the main body 40 to be connected to the first to seventh terminals 311 to 317, and may each have the other end connected to the printed circuit board 422.

Further, it is preferable that a layout of the first to seventh terminals 311 to 317 and a layout of the eighth to fourteenth terminals 411 to 417 correspond to each other or are the same as each other.

However, the first terminal portion 310 may also include only a single terminal coupled to the connection plate 320 implemented by a substrate, and the second terminal portion 410 may also include only a single terminal coupled to the printed circuit board 422.

Figure 9:
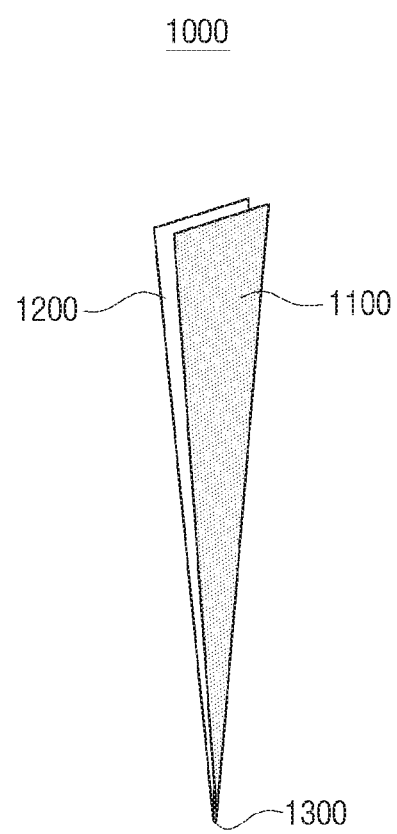
FIG. 9 is a perspective view of a bio sensor according to an embodiment of the disclosure.
Figure 10A:
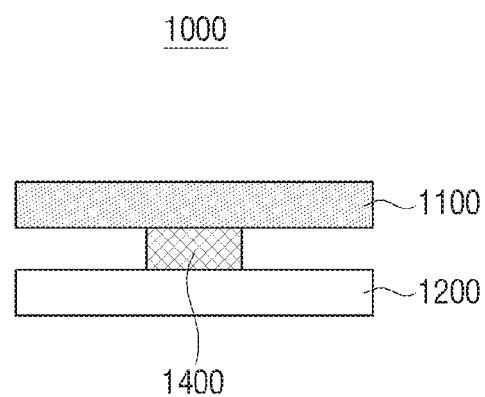
FIG. 10a is a plan view of the bio sensor illustrated in FIG. 9.

FIG. 9 is a perspective view of a bio sensor 1000 according to an embodiment of the disclosure, and FIG. 10a is a plan view of the bio sensor 1000 illustrated in FIG. 9.

Hereinafter, the bio sensor 1000 according to an embodiment of the disclosure will be described in detail with reference to FIGS. 9 and 10a.

The bio sensor 1000 may be the needle sensors 100, 100', and 300 illustrated in FIGS. 1 to 8, and the needle sensors 100, 100', and 300 illustrated in FIGS. 1 to 8 may be implemented by the bio sensor 1000 described below.

As illustrated in FIG. 9, the bio sensor 1000 includes a first electrode portion 1100, and a second electrode portion 1200 facing the first electrode portion 1100 with a space therebetween.

The bio sensor 1000, which is an electrochemical sensor, may measure a ratio of components contained in an analyte (blood or body fluid), a presence or absence a specific component, a concentration of a specific component, and the like by measuring an electric current flowing between the first and second electrode portions 1100 and 1200.

Specifically, any one of the first and second electrode portions 1100 and 1200 may be implemented as a working electrode and the other one of the first and second electrode portions 1100 and 1200 may be implemented as a counter electrode to thereby detect a flow (that is, electric current) or a presence (that is, voltage) of electrons generated by electrochemical oxidation or reduction of the analyte.

Further, any one of the first and second electrode portions 1100 and 1200 may include a reagent layer such as an enzyme layer, and in this case, the bio sensor 1000 may be implemented as an enzymatic sensor.

In this case, the reagent layer may include at least one of a glucose oxidase, a glucose dehydrogenase, a cholesterol oxidase, a cholesterol esterase, a lactate oxidase, an ascorbate oxidase, an alcohol oxidase, an alcohol dehydrogenase, a bilirubin oxidase, or a sugar dehydrogenase.

Further, the bio sensor 1000 may also be implemented as a non-enzymatic sensor that does not including a separate reagent layer.

As such, the bio sensor 1000 may detect a concentration (blood glucose) of glucose, a concentration of a specific hormone, a concentration of nicotine, a concentration of a specific antigen or antibody, or the like in an analyte such as body fluid and blood.

As illustrated in FIG. 9, the first electrode portion 1100 and the second electrode portion 1200 constituting the bio sensor 1000 may be implemented by facing type electrodes that are disposed to face each other with a predetermined space therebetween.

Further, one ends (distal end portions) of the first and second electrode portions 1100 and 1200 are sharp, and thus the first and second electrode portions 1100 and 1200 may be easily inserted into the skin due to the sharp ends.

As such, the bio sensor 1000 according to an embodiment of the disclosure is implemented as a needle sensor that is insertable into the skin, and the first electrode portion 1100 and the second electrode portion 1200 are disposed to face each other, and thus it is possible to decrease an entire length of the bio sensor 1000.

Further, the bio sensor 1000 according to the disclosure may have a relatively smaller length as compared to the bio sensor according to the related art in which a working electrode and a counter electrode are on the same plane. Further, as the first and second electrode portions 1100 and 1200 of the bio sensor 1000 are disposed to face each other, a speed (reaction speed) of measurement for an analyte may be increased.

Further, the bio sensor 1000 including the first and second electrode portions 1100 and 1200 facing each other is a needle-type sensor and is inserted into the skin, and thus it is preferable that a thickness of the bio sensor 1000 is 400 μm or less to ease pain at the time of insertion. As a specific example, the illustrated bio sensor 1000 may have a length of 14 mm and a thickness of 400 μm.

Further, the first electrode portion 1100 and the second electrode portion 1200 may be connected to each other through a connection portion 1300 having an insulating property, and the connection portion 1300 may be sharp and form a distal end of the bio sensor 1000 to be inserted into the skin.

Further, the first and second electrode portions 1100 and 1200 may be formed by folding a thin film substrate to make a pair of first and second electrode patterns printed on the thin film substrate at a predetermined interval face each other, to thereby decrease the thickness of the bio sensor 1000. The first and second electrode patterns may be carbon ink screen-printed on the thin film substrate. In this case, the connection portion 1300 may be a part of the thin film substrate between the first electrode portion 1100 and the second electrode portion 1200.

A detailed method for manufacturing the bio sensor 1000 illustrated in FIG. 9 will be described later with reference to FIGS. 11 to 12c.

As illustrated in FIG. 10a, the bio sensor 1000 may include at least one spacer 1400 disposed between the first electrode portion 1100 and the second electrode portion 1200.

Contact between the first and second electrode portions 1100 and 1200 needs to be prevented to allow the first and second electrode portions 1100 and 1200 to function as a working electrode and a counter electrode, respectively, and a short circuit may occur in the case where the first electrode portion 1100 and the second electrode portion 1200 come into contact with each other in a process of inserting the bio sensor 1000 into the skin.

The spacer 1400 is a component for preventing the first electrode portion 1100 and the second electrode portion 1200 facing each other from coming into contact with each other. To this end, the spacer 1400 may be disposed at a central portion between the first electrode portion 1100 and the second electrode portion 1200, and may have a pin shape or a rod shape extending along a length direction of the first and second electrode portions 1100 and 1200.

In addition, the spacer 1400 may support the first electrode portion 1100 and the second electrode portion 1200 while keeping a predetermined space between the first electrode portion 1100 and the second electrode portion 1200.

Further, the spacer 1400 having an insulating property may be formed of a thermoplastic adhesive such as a hot melt adhesive, or a plastic injection-molded product, and a shape and a material of the spacer 1400 may be variously changed.

Figure 10B:
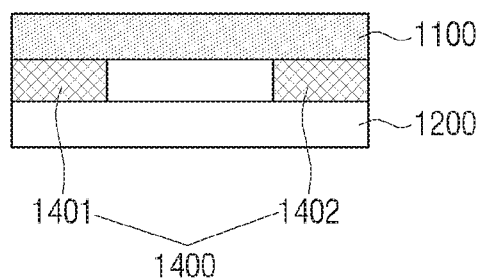

FIG. 10b is a plan view illustrating a modified example of the bio sensor illustrated in FIG. 10a.

As illustrated in FIG. 10b, a plurality of spacers 1401 and 1402 may be disposed between a first electrode portion 1100 and a second electrode portion 1200 of a bio sensor 1000a facing each other, such that it is possible to more firmly support the first and second electrode portions 1100 and 1200.

Further, the plurality of spacers 1401 and 1402 may be disposed adjacent to opposite ends of the first and second electrode portions 1100 and 1200, respectively, to more effectively prevent the first electrode portion 1100 and the second electrode portion 1200 from coming into contact with each other.

Figure 10C:
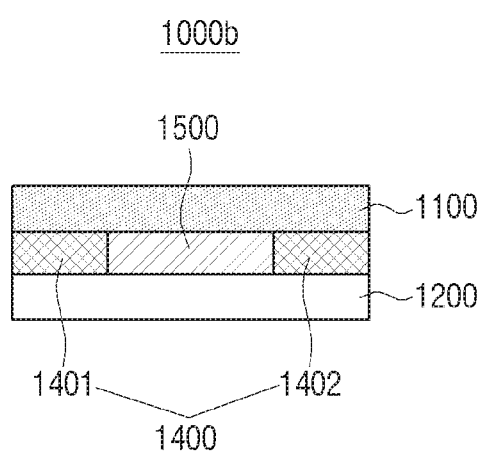
Figure 10D:
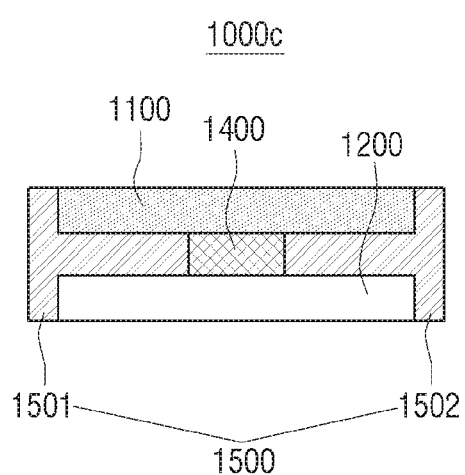

FIG. 10c is a plan view illustrating another modified example of the bio sensor illustrated in FIG. 10a, FIG. 10d is a plan view illustrating still another modified example of the bio sensor illustrated in FIG. 10a.

Referring to FIGS. 10c and 10d, a bio sensor 1000b or 1000c may further include at least one support member 1500 disposed between a first electrode portion 1100 and a second electrode portion 1200.

The at least one support member 1500 may be disposed between the first electrode portion 1100 and the second electrode portion 1200, similarly to the spacer 1400, to improve rigidity of the bio sensor 1000b or 1000c.

Specifically, the support member 1500 may have a pin shape or a rod shape extending along a length direction of the first and second electrode portions 1100 and 1200, and may be formed of a metal material such as stainless steel to increase rigidity of the bio sensor 1000b or 1000c.

The rigidity of the bio sensor 1000b or 1000c is maintained by the support member 1500 in a process of inserting the needle-type bio sensor 1000b or 1000c having a small thickness into the skin, and thus it is possible to easily insert the bio sensor 1000b or 1000c into the skin. Further, it is possible to prevent the first and second electrode portions 1100 and 1200 from being bent or being deformed in the process of inserting the bio sensor 1000b or 1000c into the skin.

In addition, the support member 1500 may be separably coupled to the bio sensor 1000b or 1000c. In this case, the support member 1500 may be removed after the bio sensor 1000b or 1000c is inserted into the skin.

The support member 1500 may be separated from the bio sensor 1000b or 1000c by the sensor module releasing pin 260 illustrated in FIGS. 1 and 2 in a state in which the bio sensor 1000b or 1000c (or the needle sensor 100 of FIG. 5) is inserted into the skin, and may be taken out to the outside of the main body 20 by the sensor module releasing pin 260.

As such, the support member 1500 is removed after the bio sensor 1000b or 1000c is inserted into the skin, such that it is possible to ease an uncomfortable feeling or pain of the user that may be caused by the insertion of the bio sensor 1000b or 1000c even in the case where detection of a bio signal is continuously performed for a predetermined period in a state in which the bio sensor 1000b or 1000c is inserted into the skin.

Further, one support member 1500 may be disposed between the plurality of spacers 1401 and 1402 as illustrated in FIG. 10c. In addition, the support member 1500 may include a pair of support members 1501 and 1502 as illustrated in FIG. 10d, and the pair of support members 1501 and 1502 may be disposed while having the spacer 1400 interposed therebetween.

The pair of support members 1501 and 1502 may be disposed between the first electrode portion 1100 and the second electrode portion 1200 and may cover opposite ends of the first and second electrode portions 1100 and 1200, respectively, such that it is possible to further increase the rigidity of the bio sensor 1000c.

The structures of the spacer 1400 and the support member 1500 disposed between the first and second electrode portions 1100 and 1200 may be variously changed.

Figure 11:
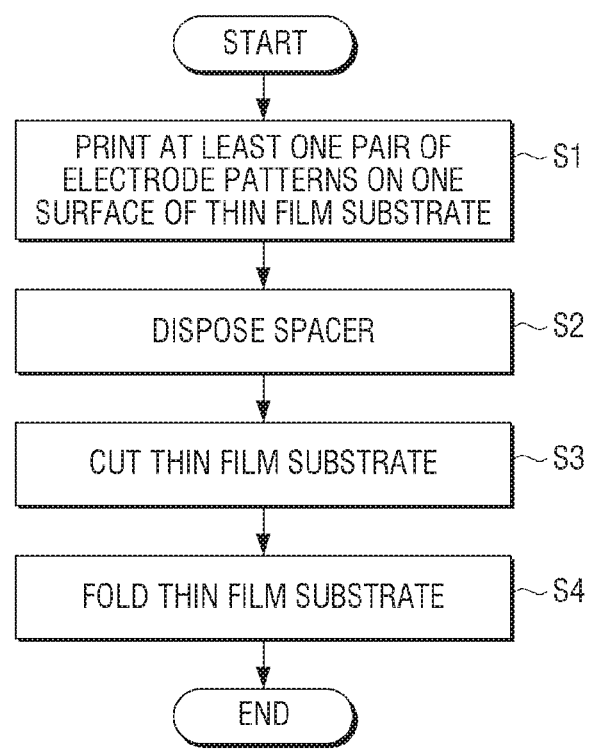
FIG. 11 is a flowchart illustrating a method for manufacturing the bio sensor illustrated in FIG. 9.

FIG. 11 is a flowchart illustrating a method for manufacturing the bio sensor 1000 illustrated in FIG. 9, and FIGS. 12a to 12c are views for describing the method for manufacturing the bio sensor illustrated in FIG. 11.

Hereinafter, the method for manufacturing the bio sensor 1000 according to an embodiment of the disclosure will be described with reference to FIGS. 11 to 12c.

The bio sensor 1000 is inserted into the skin and thus needs to have a small thickness to ease an uncomfortable feeling or pain of the user, and it is preferable that the thickness of the bio sensor 1000 is about 400 μm or less.

In the method for manufacturing the ultra-thin bio sensor 1000 according to an embodiment of the disclosure, first, at least one pair of electrode patterns is printed on one surface of a thin film substrate B (S1).

The thin film substrate B may be a flexible substrate having a thickness of 100 μm or less, and may be a sheet capable of being easily bent in a process of manufacturing the bio sensor 1000. Further, the thin film substrate B may be formed of a material having an insulating property.

At least one pair of electrode patterns 1101 and 1201 formed of carbon ink or the like is printed on the one surface of the thin film substrate B, and the electrode patterns printed on the thin film substrate B may be printed through screen printing.

Figure 12A:
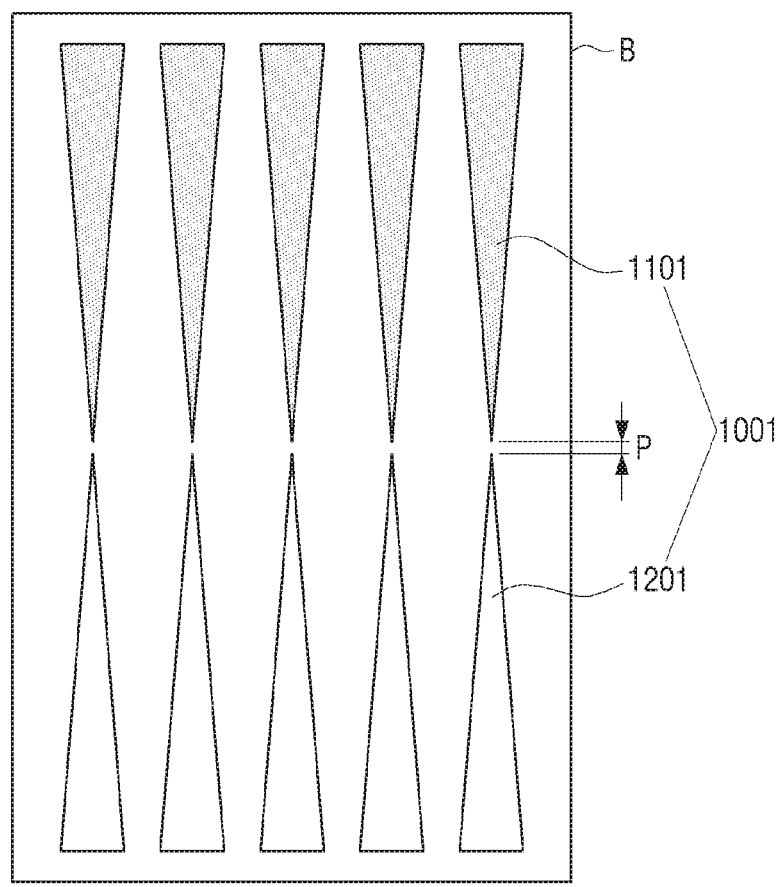
FIGS. 12a to 12c are views for describing the method for manufacturing a bio sensor illustrated in FIG. 11.

It is possible to mass produce the bio sensors 1000 by printing a plurality of pairs of electrode patterns 1101 and 1201 on the one surface of the thin film substrate B as illustrated in FIG. 12a.

The pair of electrode patterns 1101 and 1201 may be a pair of first and second electrode patterns 1101 and 1201 of which one ends facing each other are sharp. Further, the first electrode pattern 1101 and the second electrode pattern 1201 may be printed so that the one ends that are sharp and face each other are spaced apart from each other at a predetermined interval P.

In addition, shapes of the first and second electrode patterns 1101 and 1201 may be symmetric with respect to the one ends facing each other.

Next, the spacer 1400 is disposed on at least one of the pair of electrode patterns 1101 and 1201 (S2).

Figure 12B:
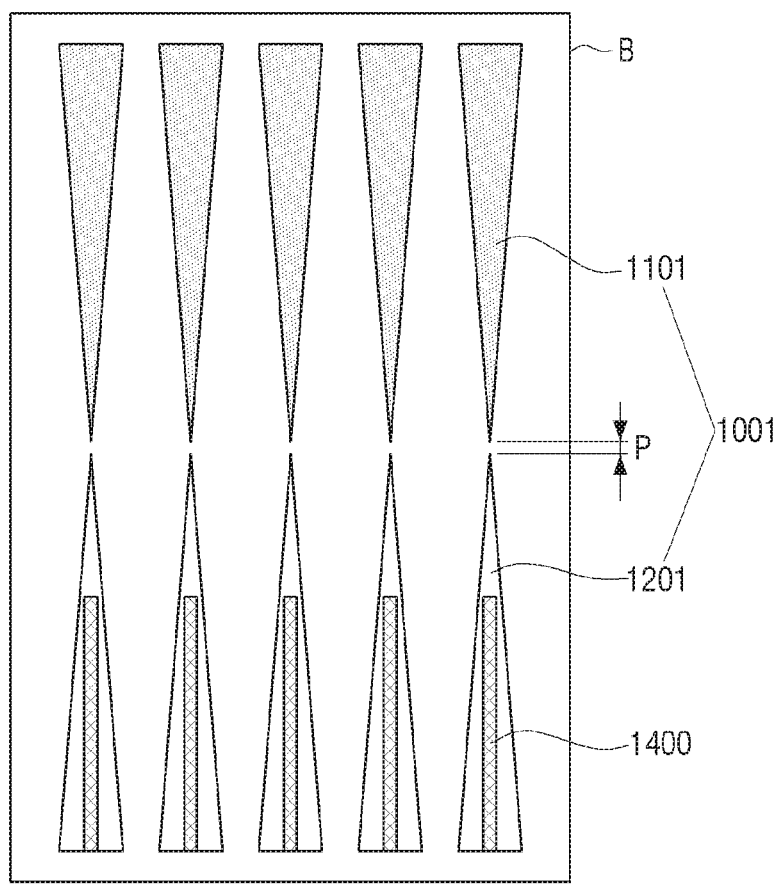

As illustrated in FIG. 12b, the spacer 1400 may be disposed on at least one of each of the plurality of pairs of electrode patterns 1101 and 1201 printed on the one surface of the thin film substrate B. As a result, the spacer 1400 may prevent the first electrode pattern 1101 and the second electrode pattern 1201 from coming into contact with each other as the thin film substrate B is folded so that the first electrode pattern 1101 and the second electrode pattern 1201 face each other later.

As described above, the spacer 1400 having an insulating property may be formed of a thermoplastic adhesive such as a hot melt adhesive, or a plastic injection-molded product, and may have a pin shape or a rod shape extending along a length direction of the electrode pattern.

Further, the spacer 1400 may be formed by applying an adhesive such as a hot melt adhesive onto the electrode pattern 1101 or 1201, thereby making it possible to rapidly and easily dispose the spacer 1400 on multiple electrode patterns 1101 or 1201.

Next, the thin film substrate B is cut in the shapes of the pair of electrode patterns 1101 and 1201 (S3).

Figure 12C:
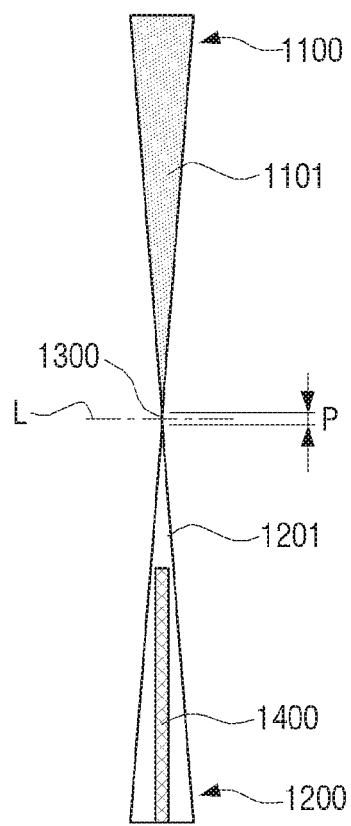

The pair of first and second electrode patterns 1101 and 1201 constitute one bio sensor 1000, and thus the multiple first and second electrode patterns 1101 and 1201 printed on the thin film substrate B may be cut in pairs of the first and second electrode patterns 1101 and 1201 as illustrated in FIG. 12c.

Further, the one ends of the first electrode pattern 1101 and the second electrode pattern 1201 may be spaced apart from each other at the predetermined interval P and connected to each other through the connection portion 1300 as illustrated in FIG. 12c.

The connection portion 1300 may be a part of the thin film substrate B with no electrode pattern printed, the part being disposed between the first and second electrode patterns 1101 and 1201.

Next, the cut thin film substrate B is folded at a portion between the one end of the first electrode pattern 1101 and the one end of the second electrode pattern 1201 to make the first electrode pattern 1101 and the second electrode pattern 1201 face each other (S4).

Specifically, the first electrode pattern 1101 and the second electrode pattern 1201 are spaced apart from each other at the predetermined interval P as illustrated in FIG. 12c. Therefore, the first and second electrode patterns 1101 and 1201 face each other by folding the thin film substrate B in half along a center line L of the connection portion 1300 disposed between the one ends of the first and second electrode patterns 1101 and 1201 facing each other. As a result, the first and second electrode patterns 1101 and 1201 may be implemented as the first and second electrode portions 1100 and 1200 facing each other.

As such, the bio sensor 1000 in which the first and second electrode portions 1100 and 1200 face each other may be manufactured by folding the thin film substrate B so that the first and second electrode patterns 1101 and 1201 screen-printed on the one surface of the thin film substrate B face each other. Further, the shape of the bio sensor 1000 may be variously changed by printing various shapes of electrode patterns on the thin film substrate B through screen printing.

Further, the first and second electrode portions 1100 and 1200 are formed by printing multiple electrode patterns 1101 and 1201 on the thin film substrate B, and thus it is possible to mass produce the bio sensors 1000 each having a thickness of 400 μm or less with a simple manufacturing process.

An order of the respective steps in the method for manufacturing a bio sensor described above may be changed or some of the steps may be omitted or repeated.

Figure 13:
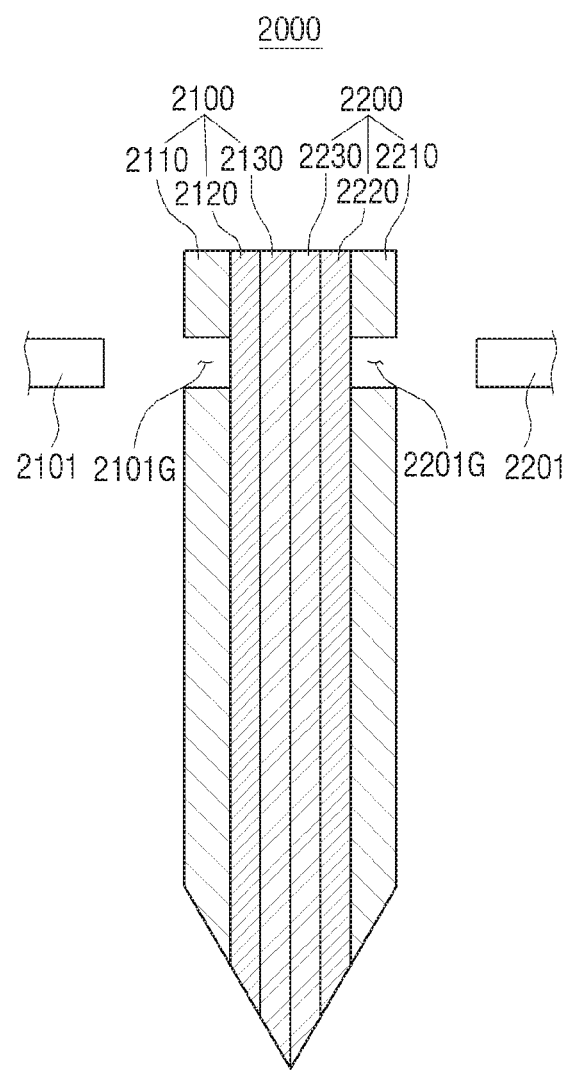
FIG. 13 is a side cross-sectional view of a bio sensor according to another embodiment of the disclosure.

FIG. 13 is a side cross-sectional view of a bio sensor 2000 according to another embodiment of the disclosure.

The bio sensor 2000 is a needle sensor coupled to the sensor module 10, 10', or 30 of the apparatus 1, 1', or 2 for measuring bio signals illustrated in FIGS. 1 to 8, and a distal end portion of the bio sensor 2000 may be sharp.

As illustrated in FIG. 13, the bio sensor 2000 includes a first electrode portion 2100 and a second electrode portion 2200.

The bio sensor 2000 is an electrochemical sensor, and any one of the first and second electrode portions 2100 and 2200 may be implemented as a working electrode and the other one may be implemented as a counter electrode.

Further, the first electrode portion 2100 includes a first substrate 2110, a first electrode layer 2120, and a dielectric layer 2130 which are sequentially laminated, and the second electrode portion 2200 includes a second substrate 2210, a second electrode layer 2220, and a reagent layer 2230 which are sequentially laminated.

The first electrode portion 2100 and the second electrode portion 2200 are laminated to make the dielectric layer 2130 and the reagent layer 2230 be in contact with each other.

Therefore, the first electrode portion 2100 and the second electrode portion 2200 may be insulated from each other by the dielectric layer 2130 even in the case where the first electrode portion 2100 and the second electrode portion 2200 are in contact with each other.

Further, the first electrode portion 2100 has a first connector groove 2101G and includes a first connector 2101 inserted into the first connector groove 2101G and electrically connected to the first electrode layer 2120. Further, the second electrode portion 2200 has a second connector groove 2201G and includes a second connector 2201 inserted into the second connector groove 2201G and electrically connected to the second electrode layer 2220.

As illustrated in FIG. 13, the first connector groove 2101G may penetrate through the first substrate 2110 disposed at one outermost side of the bio sensor 2000 to expose the first electrode layer 2120 to the outside, and the second connector groove 2201G may penetrate through the second substrate 2210 disposed at the other outermost side of the bio sensor 2000 to expose the second electrode layer 2220 to the outside.

As a result, the bio sensor 2000 may be electrically connected to the first terminal portion 110 or the connection plate 120 of the sensor module 10 illustrated in FIG. 1 through the first and second connectors 2101 and 2201.

The bio sensor 2000 according to another embodiment of the disclosure may be mass produced by sequentially laminating the first substrate 2110, the first electrode layer 2120, the dielectric layer 2130, the reagent layer 2230, the second electrode layer 2220, and the second substrate 2210 each of which has a plate shape, cutting the first substrate 2110, the first electrode layer 2120, the dielectric layer 2130, the reagent layer 2230, the second electrode layer 2220, and the second substrate 2210, in a shape of the bio sensor 2000, forming the first and second connector grooves 2101G and 2201G by perforation, and coupling the first and second connectors 2101 and 2201 to the first and second connector grooves 2101G and 2201G, respectively.

Figure 14A:
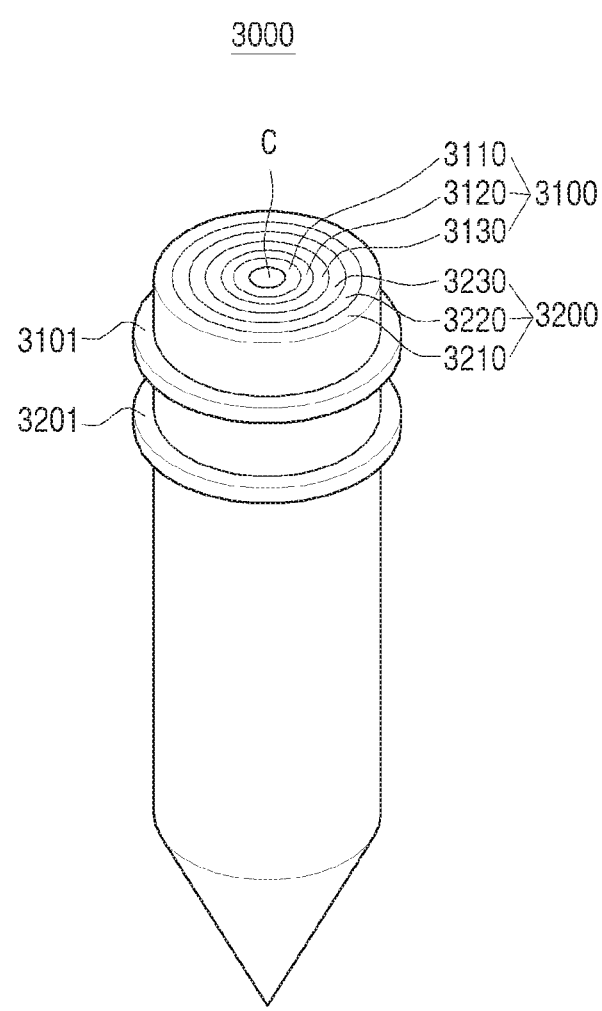
FIG. 14a is a perspective view of a bio sensor according to still another embodiment of the disclosure.
Figure 14B:
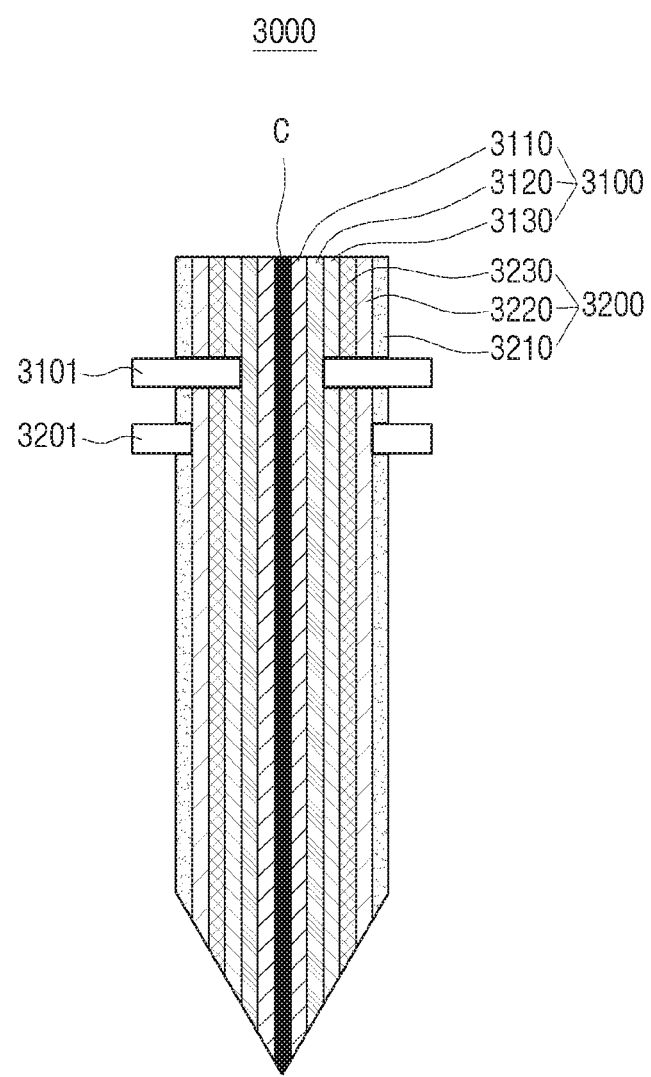

FIG. 14a is a perspective view of a bio sensor 3000 according to still another embodiment of the disclosure, and FIG. 14b is a side cross-sectional view of the bio sensor 3000 illustrated in FIG. 14a.

A configuration of the bio sensor 3000 illustrated in FIGS. 14a and 14b is similar to that of the bio sensor 2000 illustrated in FIG. 13, and thus an overlapping description will be omitted.

As illustrated in FIGS. 14a and 14b, the bio sensor 3000 may be a needle sensor having a cylindrical shape with a sharp distal end portion and coupled to the sensor module 10, 10', or 30 of the apparatus 1, 1', or 2 for measuring bio signals illustrated in FIGS. 1 to 8.

The bio sensor 3000 may have a structure in which a first substrate 3110, a first electrode layer 3120, and a dielectric layer 3130 that constitute a first electrode portion 3100, and a reagent layer 3230, a second electrode layer 3220, and a second substrate 3210 that constitute a second electrode portion 3200 are sequentially laminated from the center of the bio sensor 3000 toward the outside.

Further, a cross section of the bio sensor 3000 taken along a direction perpendicular to a length direction may have a concentric circle shape in which the first substrate 3110, the first electrode layer 3120, the dielectric layer 3130, the reagent layer 3230, the second electrode layer 3220, and the second substrate 3210 are sequentially laminated from the center of the bio sensor 3000 toward the outside.

Further, the bio sensor 3000 having the above-described structure may be manufactured by sequentially coupling the first substrate 3110, the first electrode layer 3120, and the dielectric layer 3130, and the reagent layer 3230, the second electrode layer 3220, and the second substrate 3210 that constitute the second electrode portion 3200 to a cylindrical central member C disposed at the center.

For example, the bio sensor 3000 may be manufactured by sequentially coating a side surface of the central member C with the first substrate 3110, the first electrode layer 3120, and the dielectric layer 3130, and the reagent layer 3230, the second electrode layer 3220, and the second substrate 3210 that constitute the second electrode portion 3200, and the central member C may be formed of a plastic material having an insulating property.

Further, the central member C may function as the support member 1500 illustrated in FIGS. 10c and 10d, and may be removed after the bio sensor 3000 is inserted into the skin.

As illustrated in FIG. 14b, first and second connector grooves that are concave may be formed in a side surface of the bio sensor 3000 along an outer circumferential surface of the bio sensor 3000, and first and second connectors 3101 and 3201 each having a ring shape may be inserted into and coupled to the first and second connector grooves, respectively.

As illustrated in FIG. 14b, the first connector groove may penetrate inwardly from the second substrate 3210 disposed at the outermost side of the bio sensor 3000 to expose the first electrode layer 3120 to the outside. Further, the second connector groove may penetrate inwardly from the second substrate 3210 to expose the second electrode layer 3220 to the outside.

As a result, the bio sensor 3000 may be electrically connected to the first terminal portion 110 or the connection plate 120 of the sensor module 10 illustrated in FIG. 1 through the first and second connectors 3101 and 3201.

Further, the first and second connectors 3101 and 3201 are inserted and coupled inwardly from the outer circumferential surface of the bio sensor 3000, and thus the first connector 3101 may further include an insulating layer covering a portion of the first connector 3101 that is in contact with the dielectric layer 3130, the reagent layer 3230, the second electrode layer 3220, and the second substrate 3210 that are disposed outside the first electrode layer 3120. Further, the second connector 3201 may further include an insulating layer covering a portion of the second connector 3201 that is in contact with the second substrate 3210 disposed outside the second electrode layer 3220.

By doing so, the first connector 3101 may be electrically connected only to the first electrode layer 3120, and the second connector 3201 may be electrically connected only to the second electrode layer 3220. As a result, it is possible to prevent the first substrate 3110, the first electrode layer 3120, and the dielectric layer 3130, and the reagent layer 3230, the second electrode layer 3220, and the second substrate 3210 that constitute the second electrode portion 3200 are short circuited by the first and second connectors 3101 and 3201.

Figure 14C:
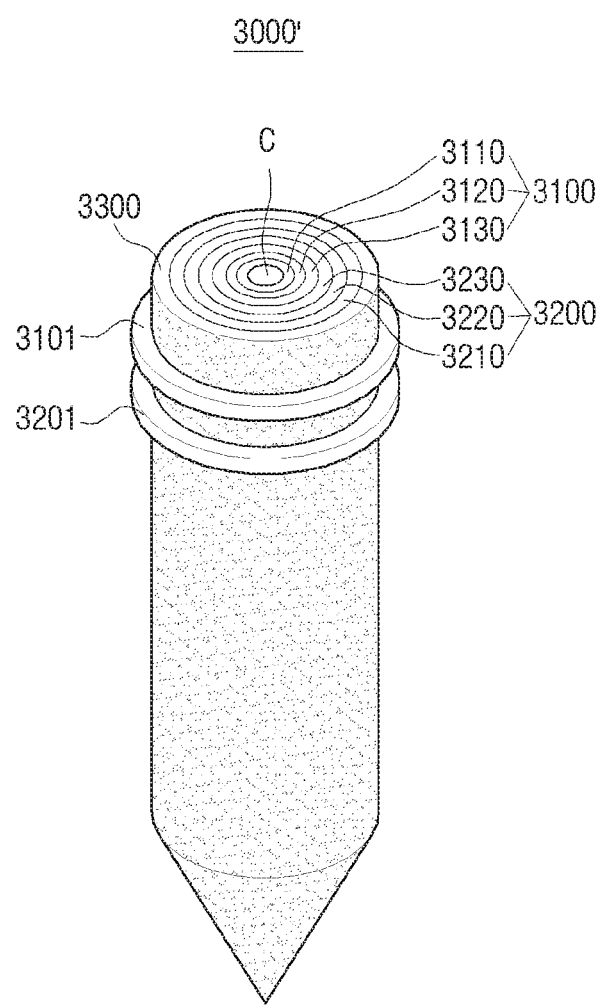

FIG. 14c is a perspective view illustrating a modified example of the bio sensor illustrated in FIG. 14a.

As illustrated in FIG. 14c, a bio sensor 3000' may further include a coating layer 3300 disposed at the outermost side thereof, and the coating layer 3300 may be formed of a material such as polydioxanone (PDO).

The coating layer 3300 may increase rigidity of the bio sensor 3000' in a process of inserting the bio sensor 3000' into the skin, and the coating layer 3300 may be melted and absorbed into the body after the bio sensor 3000' is inserted into the skin. Therefore, the bio sensor 3000' may be easily inserted into the skin without a separate support member or a catheter.

Although various embodiments of the present disclosure have been individually described hereinabove, the respective embodiments are not necessarily implemented singly, but may also be implemented so that configurations and operations thereof are combined with those of one or more other embodiments.

Although the embodiments of the disclosure have been illustrated and described hereinabove, the present disclosure is not limited to the specific embodiments described above, but may be variously modified by those skilled in the art to which the disclosure pertains without departing from the scope and spirit of the disclosure as claimed in the claims. These modifications should also be understood to fall within the technical spirit and scope of the disclosure.

The invention claimed is:

1. An apparatus for measuring bio signals, comprising:
a sensor module configured to include a needle sensor to be inserted into a skin; and
a main body to which the sensor module is separably coupled and which is configured to include a controller controlling the sensor module to measure a bio signal through the needle sensor, once the sensor module is coupled,
wherein the needle sensor includes first and second electrode portions to be inserted into the skin,
wherein the first electrode portion includes a first substrate, a first electrode layer, and a dielectric layer which are sequentially laminated,
the second electrode portion includes a second substrate, a second electrode layer, and a reagent layer which are sequentially laminated, and
the first and second electrode portions are laminated to make the dielectric layer and the reagent layer be in contact with each other.

2. The apparatus for measuring bio signals as claimed in claim 1, wherein the sensor module includes a first terminal portion connected to the needle sensor, and
the main body includes a second terminal portion electrically connecting the first terminal portion and the controller to each other through coupling of the sensor module.

3. The apparatus for measuring bio signals as claimed in claim 2, wherein the main body has a coupling groove which is formed in a bottom surface of the main body and into which the sensor module is inserted, and
the second terminal portion is disposed in the coupling groove.

4. The apparatus for measuring bio signals as claimed in claim 3, wherein the sensor module includes a first magnet portion, and
the main body includes a second magnet portion attached to the first magnet portion to allow the sensor module inserted into the main body to be in position.

5. The apparatus for measuring bio signals as claimed in claim 2, wherein the main body has a coupling hole penetrating through the main body to allow the sensor module to be inserted, the first terminal portion is disposed at a side surface of the sensor module, and the second terminal portion is disposed at an inner circumferential surface of the coupling hole.

6. The apparatus for measuring bio signals as claimed in claim 5, wherein the sensor module includes a first magnet portion, and the main body includes a second magnet portion attached to the first magnet portion to allow the sensor module inserted into the main body to be in position.

7. The apparatus for measuring bio signals as claimed in claim 1, wherein the main body includes at least one auxiliary sensor disposed in a bottom surface of the main body.

8. The apparatus for measuring bio signals as claimed in claim 1, wherein the controller measures an electric current flowing between the first electrode portion and the second electrode portion.

9. A bio sensor to be inserted into a skin, comprising:

a first electrode portion of which one end is sharp; and a second electrode portion configured to face the first electrode portion with a space therebetween and of which one end is sharp, wherein the first electrode portion includes a first substrate, a first electrode layer, and a dielectric layer which are sequentially laminated, the second electrode portion includes a second substrate, a second electrode layer, and a reagent layer which are sequentially laminated, and the first and second electrode portions are laminated to make the dielectric layer and the reagent layer be in contact with each other.

10. The bio sensor as claimed in claim 9, further comprising at least one spacer disposed between the first electrode portion and the second electrode portion.

11. The bio sensor as claimed in claim 10, further comprising a support member separably disposed between the first electrode portion and the second electrode portion and supporting the first and second electrode portions.

12. The bio sensor as claimed in claim 9, wherein the first and second electrode portions are formed by folding a thin film substrate to make first and second electrode patterns printed on the thin film substrate at a predetermined interval face each other.

13. The bio sensor as claimed in claim 9, wherein the first electrode portion has a first connector groove and includes a first connector inserted into the first connector groove and electrically connected to the first electrode layer, and the second electrode portion has a second connector groove and includes a second connector inserted into the second connector groove and electrically connected to the second electrode layer.

14. A method for manufacturing a bio sensor, comprising:

printing at least one pair of electrode patterns on one surface of a thin film substrate;

disposing a spacer on at least one of the pair of electrode patterns;

cutting the thin film substrate in a shape of the pair of electrode patterns; and folding the cut thin film substrate, wherein the electrode pattern includes first and second electrode portions to be inserted into a skin, wherein the first electrode portion includes a first substrate, a first electrode layer, and a dielectric layer which are sequentially laminated, the second electrode portion includes a second substrate, a second electrode layer, and a reagent layer which are sequentially laminated, and the first and second electrode portions are laminated to make the dielectric layer and the reagent layer be in contact with each other.

15. The method for manufacturing a bio sensor as claimed in claim 14, wherein in the printing, at least one pair of first and second electrode patterns of which one ends are spaced apart from each other at a predetermined interval is printed, the one ends being sharp and facing each other, and in the folding, the thin film substrate is folded at a portion between the one end of the first electrode pattern and the one end of the second electrode pattern to make the first electrode pattern and the second electrode pattern face each other.

\* \* \* \* \*